United States Patent
Ryotokuji

(10) Patent No.: US 10,213,333 B2
(45) Date of Patent: Feb. 26, 2019

(54) METHOD OF CONTROLLING IMMUNE CELLS

(71) Applicant: Kenji Ryotokuji, Chiba (JP)

(72) Inventor: Kenji Ryotokuji, Chiba (JP)

(*) Notice: Subject to any disclaimer, the term of this patent is extended or adjusted under 35 U.S.C. 154(b) by 580 days.

(21) Appl. No.: 14/821,150

(22) Filed: Aug. 7, 2015

(65) Prior Publication Data
US 2016/0242954 A1 Aug. 25, 2016

Related U.S. Application Data

(63) Continuation-in-part of application No. 13/551,730, filed on Jul. 18, 2012, now Pat. No. 9,358,180.

(60) Provisional application No. 62/035,103, filed on Aug. 8, 2014, provisional application No. 61/635,359, filed on Apr. 19, 2012, provisional application No. 61/526,089, filed on Aug. 22, 2011, provisional application No. 61/508,883, filed on Jul. 18, 2011.

(51) Int. Cl.
*A61F 7/00* (2006.01)
*A61H 39/06* (2006.01)
*A61H 39/04* (2006.01)
*A61N 2/00* (2006.01)
*A61N 5/06* (2006.01)

(52) U.S. Cl.
CPC ............ *A61F 7/007* (2013.01); *A61H 39/04* (2013.01); *A61H 39/06* (2013.01); *A61F 2007/0045* (2013.01); *A61F 2007/0047* (2013.01); *A61F 2007/0096* (2013.01); *A61H 2201/0207* (2013.01); *A61H 2201/0221* (2013.01); *A61H 2201/10* (2013.01); *A61H 2201/5007* (2013.01); *A61H 2201/5092* (2013.01); *A61H 2205/125* (2013.01); *A61H 2230/255* (2013.01); *A61H 2230/505* (2013.01); *A61N 2/002* (2013.01); *A61N 5/0619* (2013.01)

(58) Field of Classification Search
CPC ...................................................... A61H 39/06
See application file for complete search history.

(56) References Cited

U.S. PATENT DOCUMENTS

| | | | |
|---|---|---|---|
| 5,950,635 A | 9/1999 | Garcia-Rill et al. | |
| 2003/0055475 A1* | 3/2003 | Rousmaniere | A61F 7/034 607/114 |
| 2005/0288744 A1* | 12/2005 | Pilla | A61H 39/002 607/86 |
| 2006/0195168 A1* | 8/2006 | Dunbar | A61F 7/007 607/108 |
| 2011/0034782 A1* | 2/2011 | Sugimachi | A61H 39/04 600/301 |

* cited by examiner

*Primary Examiner* — Kaitlyn Smith
(74) *Attorney, Agent, or Firm* — Westerman, Hattori, Daniels & Adrian, LLP

(57) ABSTRACT

A method for regulating immune cells includes applying a stimulus to a specific area to be stimulated at a body surface by a stimulus applying apparatus so as to bring an increase rate of a blood flow to 60% or more, preferably, 100% or more. The blood flow is measured by a laser Doppler tissue blood flow meter attached to a central part of an inner side of a wrist joint. The regulating and balancing these T cell groups finely is essential to maintain the immune system of human beings and increase in blood flow volume by thermal therapy enables a regulatory T cell to regulate and balance the immune cells.

2 Claims, 20 Drawing Sheets

First

| 10:00 | :05 | :10 | :15 | :20 | | :35 | :45 | rest supine position measurement 1    blood sampling 1    stimulation    measurement 2

Second

| 10:00 | :05 | :10 | :15 | :20 | rest supine position measurement 3    blood sampling 2

FIG. 10A

Stimulated location: Chu Kyoku Ketsu or points

| Patient No. | Sex | Age of patient | lymphocyte in blood cells (R1) | CD127Lo CD25+ in lymphocyte | CD127Lo CD25+ in CD4+lymphocyte | CD4 in lymphocyte | CD8 in lymphocyte | CD4/CD8 ratio in lymphocyte |
|---|---|---|---|---|---|---|---|---|
| Patient 31: | Male | 44 | 0.64 | 0.74 | 0.69 | 1.16 | 0.94 | 1.24 |
| Patient 32: | Male | 19 | 1.24 | 0.77 | 0.71 | 1.07 | 0.93 | 1.16 |
| Patient 33: | Male | 18 | 1.14 | 0.88 | 1.01 | 1.05 | 0.94 | 1.12 |
| Average | | 27.00 | 1.01 | 0.80 | 0.80 | 1.10 | 0.93 | 1.17 |
| SD | | 14.73 | 0.32 | 0.07 | 0.18 | 0.06 | 0.01 | 0.06 |

FIG. 11A

Stimulated location: Ken Gu Ketsu or points

| Patient No. | Sex | Age of patient | lymphocyte in blood cells (R1) | CD127Lo CD25+ in lymphocyte | CD127Lo CD25+ in CD4+lymphocyte | CD4 in lymphocyte | CD8 in lymphocyte | CD4/CD8 ratio in lymphocyte |
|---|---|---|---|---|---|---|---|---|
| Patient 1: | Male | 31 | 0.97 | 0.85 | 0.93 | 0.90 | 1.07 | 0.84 |
| Patient 2: | Male | 19 | 1.16 | 0.99 | 0.88 | 1.00 | 0.95 | 1.05 |
| Patient 3: | Male | 18 | 0.98 | 0.78 | 0.86 | 1.04 | 1.05 | 1.00 |
| Average | | 22.67 | 1.04 | 0.87 | 0.89 | 0.98 | 1.02 | 0.97 |
| SD | | 7.23 | 0.11 | 0.11 | 0.03 | 0.07 | 0.06 | 0.11 |

FIG. 12A

Stimulated location: Show Kai Ketsu or points

| Patient No. | Sex | Age of patient | lymphocyte in blood cells (R1) | CD127Lo CD25+ in lymphocyte | CD127Lo CD25+ in CD4+lymphocyte | CD4 in lymphocyte | CD8 in lymphocyte | CD4/CD8 ratio in lymphocyte |
|---|---|---|---|---|---|---|---|---|
| Patient 22: | Male | 25 | 1.04 | 1.12 | 0.93 | 1.18 | 0.82 | 1.43 |
| Patient 23: | Female | 54 | 0.96 | 0.77 | 0.92 | 1.06 | 0.94 | 1.13 |
| Patient 24: | Male | 18 | 1.57 | 0.86 | 0.76 | 1.06 | 0.99 | 1.07 |
| Average | | 32.33 | 1.19 | 0.92 | 0.87 | 1.10 | 0.92 | 1.21 |
| SD | | 19.09 | 0.33 | 0.18 | 0.09 | 0.07 | 0.09 | 0.19 |

FIG. 13A

Stimulated location: Shi In Ketsu or points

| Patient No. | Sex | Age of patient | lymphocyte in blood cells (R1) | CD127Lo CD25+ in lymphocyte | CD127Lo CD25+ in CD4+lymphocyte | CD4 in lymphocyte | CD8 in lymphocyte | CD4/CD8 ratio in lymphocyte |
|---|---|---|---|---|---|---|---|---|
| Patient 25: | Male | 38 | 0.92 | 1.35 | 1.39 | 1.07 | 0.89 | 1.20 |
| Patient 26: | Male | 19 | 1.11 | 1.26 | 1.21 | 1.02 | 0.97 | 1.05 |
| Patient 27: | Male | 18 | 0.76 | 1.27 | 1.27 | 1.14 | 0.94 | 1.20 |
| Average | | 25.00 | 0.93 | 1.29 | 1.29 | 1.08 | 0.93 | 1.15 |
| SD | | 11.27 | 0.18 | 0.05 | 0.09 | 0.06 | 0.04 | 0.09 |

FIG. 14A

Stimulated location: Ken Show Ketsu or points

| Patient No. | Sex | Age of patient | lymphocyte in blood cells (R1) | CD127Lo CD25+ in lymphocyte | CD127Lo CD25+ in CD4+lymphocyte | CD4 in lymphocyte | CD8 in lymphocyte | CD4/CD8 ratio in lymphocyte |
|---|---|---|---|---|---|---|---|---|
| Patient 28: | Male | 18 | 0.81 | 0.80 | 0.93 | 1.02 | 0.96 | 1.06 |
| Patient 29: | Male | 20 | 1.21 | 0.82 | 1.09 | 1.12 | 0.82 | 1.37 |
| Patient 30: | Female | 18 | 1.25 | 1.56 | 1.22 | 1.26 | 0.81 | 1.57 |
| Average | | 18.67 | 1.09 | 1.06 | 1.08 | 1.13 | 0.86 | 1.33 |
| SD | | 1.15 | 0.24 | 0.43 | 0.14 | 0.12 | 0.09 | 0.26 |

FIG. 15A

Stimulated location: Jin Gei Ketsu or points

| Patient No. | Sex | Age of patient | lymphocyte in blood cells (R1) | CD127Lo CD25+ in lymphocyte | CD127Lo CD25+ in CD4+lymphocyte | CD4 in lymphocyte | CD8 in lymphocyte | CD4/CD8 ratio in lymphocyte |
|---|---|---|---|---|---|---|---|---|
| Patient 7: | Female | 22 | 1.37 | 1.02 | 0.84 | 1.04 | 0.94 | 1.11 |
| Patient 8: | Male | 18 | 0.86 | 1.11 | 1.05 | 1.08 | 0.96 | 1.13 |
| Patient 9: | Female | 26 | 0.48 | 1.37 | 1.08 | 1.12 | 0.96 | 1.16 |
| Average | | 22.00 | 0.90 | 1.17 | 0.99 | 1.08 | 0.95 | 1.13 |
| SD | | 4.00 | 0.45 | 0.18 | 0.13 | 0.04 | 0.01 | 0.03 |

FIG. 16A

Stimulated location: San In Kou Ketsu or points

| Patient No. | Sex | Age of patient | lymphocyte in blood cells (R1) | CD127Lo CD25+ in lymphocyte | CD127Lo CD25+ in CD4+lymphocyte | CD4 in lymphocyte | CD8 in lymphocyte | CD4/CD8 ratio in lymphocyte |
|---|---|---|---|---|---|---|---|---|
| Patient 10: | Male | 40 | 0.61 | 1.51 | 1.29 | 1.09 | 1.09 | 1.00 |
| Patient 11: | Male | 18 | 0.46 | 1.20 | 1.11 | 1.35 | 0.93 | 1.44 |
| Patient 12: | Male | 19 | 0.89 | 0.59 | 0.75 | 1.05 | 0.96 | 1.09 |
| Average | | 25.67 | 0.65 | 1.10 | 1.05 | 1.16 | 0.99 | 1.18 |
| SD | | 12.42 | 0.22 | 0.47 | 0.28 | 0.16 | 0.08 | 0.23 |

METHOD OF CONTROLLING IMMUNE CELLS

CROSS-REFERENCES TO RELATED APPLICATION

This application is a CIP of application Ser. No. 13/551,730, now U.S. Pat. No. 9,358,180, filed Jul. 18, 2012, which claims priority to U.S. Provisional Patent Application Ser. No. 61/508,883 filed Jul. 18, 2011, U.S. Provisional Patent Application Ser. No. 61/526,089 filed Aug. 22, 2011, and U.S. Provisional Patent Application Ser. No. 61/635,359 filed Apr. 19, 2012, the contents of which are incorporated herein by reference in their entireties. This application also claims priority to U.S. Provisional Patent Application Ser. No. 62/035,103 filed Aug. 8, 2014, the contents of which are incorporated herein by reference in their entireties. This application has related application Ser. No. 14/703,021, filed May 4, 2015, which is a CIP of the same parent, application Ser. No. 13/551,730, filed Jul. 18, 2012. The contents of application Ser. No. 14/703,021, filed May 4, 2015 are incorporated herein by reference in their entireties

BACKGROUND

Technical Field

The present invention relates to a stimulus method in which stress is released in order to improve lifestyle-related diseases such as the diabetes, obesity and high blood pressure resulting from the stress, by activating a peripheral circulatory function and an autonomic nervous function through a stimulus to specific parts of a body surface by an acupuncture needle(s) or heating etc. thereby releasing the stress, and a stress-free medical treatment method based on the stimulus method.

Related Art

U.S. Pat. No. 5,950,635 discloses a point surface stimulus method according to a specific acupuncture treatment for reducing anxiousness, for example, stress. The patent discloses that LR3, HT3, and PC6 are specified as stimulus points of patients. Electrodes are brought into contact with these three stimulus points, respectively, thereby passing current through the electrode. Here, the LR3 is located on the top of the foot, at 2 cm proximal to the margin of the first and second toes. The HT3 is located on the inside of each elbow, midway between the medial end of an elbow crease and the medial epi-condyle of the humerus when the elbow is fully flexed. The PC6 is located on each wrist, 2 cm proximal to the midpoint of the wrist crease between the tendons of the palmaris longus and the flexor carpi radialis muscle. In the patent, a P1 potential is focused on with respect to at least one subcortical source, specifically in the pedunculopontine nucles (PPN), the chlinergic arm of the reticular activating system. That is, the patent discloses that when the above-mentioned stimulus points (LR3, HT3, and PC6) are stimulated with needles, the P1 potential decreases and anxiousness is reduced. In addition, other than the stimulus points LR3, HT3, and PC6, no stimulus points to be stimulated with the needles are disclosed. However, the patent discloses that, focusing on pedunculopontine nucles (PPN), anxiousness is reduced due to a decrease of the P1 potential. However, it does not discloses that due to reduction of anxiousness, it is possible to achieve effects, such as normalization of blood pressure, degression of stress, rise in body temperature, degression of neutral fat, degression of cholesterol, and an improvement of a blood sugar level due to relief of insulin resistance.

SUMMARY

By earnest research work, the present inventor found out a specific area to be stimulated, at which diabetes resulting from stress, and lifestyle-related diseases such as obesity and high blood pressure can be improved by making psychological stress free by a stimulus through acupuncture needles or heating to specific area to be stimulated of a body surface.

It is an object of the present invention to provide a body surface stimulus method for releasing psychological stress, in which stress is made free by activating a peripheral circulatory function and an autonomic nervous function by applying acupuncture needles to specific area to be stimulated of a body surface, or a stimulus based on heating etc., so that a symptom of diabetes resulting from the stress and a symptom of lifestyle-related disease such as obesity and high blood pressure may be improved.

It is another object of the present invention to provide a stress-free treatment using the body surface stimulus method for releasing the psychological stress.

According to the present invention, since a specific area to be stimulated of a body surface by acupuncture needles or heating etc. affects a homeostatic function (nerve, immunity, and endocrine system) though a peripheral circulatory function and autonomic nerves, it is possible to obtain effects, such as a normalization of blood pressure, a reduction of stress, a rise in body temperature, a degression of neutral fat, a degression of cholesterol, and an improvement of a blood sugar level due to relief of insulin resistance.

In the present invention, stimuli are, non-simultaneously and independently from each other, applied to at least one area selected according to the condition of disease, thereby achieving a reduction of psychological stress, a rise in core body temperature, a reduction of neutral fat, a reduction of cholesterol, an improvement of a blood sugar level by relief of insulin resistance, and suppression of arteriosclerosis.

In the present invention, a stimulation of a thermal stimulus pattern, which is formed by controlling an electric type heating apparatus, is non-simultaneously and independently applied to at least one areas selected according to the condition of disease, thereby achieving a reduction of psychological stress, a rise in core body temperature, a reduction of neutral fat, a reduction of cholesterol, an improvement of a blood sugar level by relief of insulin resistance, and suppression of arteriosclerosis.

In one embodiment, a stimulus treatment method for providing medical treatment by applying a stimulus to a specific area to be stimulated at a body surface by a stimulus applying apparatus so as to bring an increase rate of blood flow to 60% or more, preferably, 100% or more, wherein the blood flow is measured by a laser Doppler tissue blood flow meter attached to a central part of an inner side of a wrist joint.

The specific area may be at least one area selected from a group of os metatarsale primam 1 and 2 interosseous, os metatarsale primam 2 and 3 interosseous, and part that intersects the perpendicular line of the medial malleolus on an extension line of the medial margin on os metatarsale primam 1 and 2 in foot sole of right and left.

The specific area may be an area of a near glandula thyreoidea.

The specific area may be an area between the outer skin and a horizontal line of the inside boundary part of a hallux distal phalanx bottom and a proximal phalanx bone head in foot sole of right and left.

The stimulus may be non-simultaneously and independently applied to at least one area selected according to a condition of disease.

The stimulus applying apparatus may be a heat stimulus applying apparatus, and the heat stimulus applying apparatus forms a warm temperature stimulus pattern, wherein the stimulus pattern is made up of a thermal stimulus waveform and an interval, and the thermal stimulus waveform includes a heating waveform obtained by raising temperature to a peak temperature, 50±5 degrees Celsius by heating, and a heat release waveform formed by stopping the heating when the peak temperature is reached.

The stimulus may be selected from an acupuncture needle stimulus, a warm temperature stimulus, an optical stimulus, a magnetic stimulus, and an ultrasonic stimulus. A stress-free treatment method includes the stimulus method according to any one of the methods described above. An stimulus evaluation method includes a stimulus method according to any one of the methods described above, in which the increase rate of the blood flow is used as an indicator of the stimulus evaluation.

It is yet another object of the present invention to provide a method of regulating immune cells. One embodiment of the method for regulating immune cells includes applying a stimulus to a specific area to be stimulated at a body surface by a stimulus applying apparatus so as to bring an increase rate of a blood flow to 60% or more, preferably, 100% or more, wherein the blood flow is measured by a laser Doppler tissue blood flow meter attached to a central part of an inner side of a wrist joint, and wherein regulating and balancing these T cell groups finely is essential to maintain the immune system of human beings and increase in blood flow volume by thermal therapy enables a regulatory T cell to regulate and balance the immune cells.

In another embodiment, a method for regulating immune cells includes contacting a thermal application terminal with at least two different body sites of a body surface to apply a thermal stimulus to the body sites; and controlling the thermal stimulus to increase a blood flow by the application of the thermal stimulus to the at least two different body sites. The controlling of the thermal stimulus comprises forming a thermal stimulus pattern formed of a thermal stimulation wave form having a peak temperature which heats up a surface of the thermal application terminal to be in a range of 40 to 50° C.±5° C. and a heat release waveform to stop the heating after the peak temperature is achieved and applying the thermal stimulus pattern in thermal application modes comprising an alternative mode or a consecutive mode so as to increase the blood flow at the at least two different body sites stimulated by 60% to 150% before the thermal stimulation. The blood flow is measured by a laser Doppler tissue blood flow meter attached to a central part of an inner side of a wrist joint.

In the method for regulating immune cells described above, the specific area may be at least one area selected from the group consisting of os metatarsale primam 1 and 2 interosseous, os metatarsale primam 2 and 3 interosseous, and part that intersects the perpendicular line of the medial malleolus on an extension line of the medial margin on os metatarsale primam 1 and 2 in foot sole of right and left.

The two different body sites may include at least one area selected from the group consisting of os metatarsale primam 1 and 2 interosseous, os metatarsale primam 2 and 3 interosseous, and part that intersects the perpendicular line of the medial malleolus on an extension line of the medial margin on os metatarsale primam 1 and 2 in foot sole of right and left.

BRIEF DESCRIPTION OF THE DRAWINGS

Other features and advantages of the present stimulus method for releasing stress, and stress-free medical treatment method by the stimulus method will be apparent from the ensuing description, taken in conjunction with the accompanying drawings, in which:

FIGS. 10A and 10B are a table and diagram showing experimental data obtained by the thermal stimulation method applied to Chu Kyoku Ketsu or points according to Embodiment 4;

FIGS. 11A and 11B are a table and diagram showing another experimental data obtained by the thermal stimulation method applied to Ken Gu Ketsu or points according to Embodiment 4;

FIGS. 12A and 12B are a table and diagram showing another experimental data obtained by the thermal stimulation method applied to Show Kai Ketsu or points according to Embodiment 4;

FIGS. 13A and 13B are a table and diagram showing another experimental data obtained by the thermal stimulation method applied to Shi In Ketsu or points according to Embodiment 4;

FIGS. 14A and 14B are a table and diagram showing another experimental data obtained by the thermal stimulation method applied to Ken Show Ketsu or points according to Embodiment 4;

FIGS. 15A and 15B are a table and diagram showing another experimental data obtained by the thermal stimulation method applied to Jin Gei Ketsu or points according to Embodiment 4; and FIGS. 16A and 16B are a table and diagram showing another experimental data obtained by the thermal stimulation method applied to San In Kou Ketsu or points according to Embodiment 4.

DESCRIPTION

Figure 1:
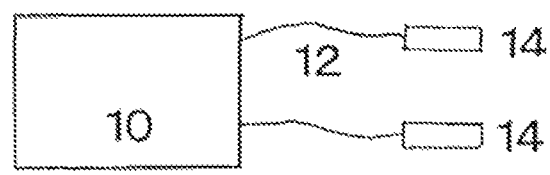
FIG. 1 is a schematic view of an electric type heating apparatus used for the present invention.

In a stimulus treatment method according to the present invention, a stimulus treatment method for providing medical treatment by applying a stimulus to a specific area to be stimulated at a body surface by a stimulus applying apparatus so as to bring an increase rate of blood flow to 60% or more, preferably, 100% or more, wherein the blood flow is measured by a laser Doppler tissue blood flow meter attached to a central part of an inner side of a wrist joint.

The specific area is at least one area selected from a group of os metatarsale primam 1 and 2 interosseous, os metatarsale primam 2 and 3 interosseous, and part that intersects the perpendicular line of the medial malleolus on an extension line of the medial margin on os metatarsale primam 1 and 2 in foot sole of right and left.

The specific area is an area of a near glandula thyreoidea.

The specific area is an area between the outer skin and a horizontal line of the inside boundary part of a hallux distal phalanx bottom and a proximal phalanx bone head in foot sole of right and left.

The stimulus is non-simultaneously and independently applied to at least one area selected according to a condition of disease.

The stimulus applying apparatus is a heat stimulus applying apparatus, and the heat stimulus applying apparatus forms a warm temperature stimulus pattern, wherein the stimulus pattern is made up of a thermal stimulus waveform and an interval, and the thermal stimulus waveform includes a heating waveform obtained by raising temperature to a peak temperature, 50±5 degrees Celsius by heating, and a heat release waveform formed by stopping the heating when the peak temperature is reached.

The stimulus is selected from an acupuncture needle stimulus, a warm temperature stimulus, an optical stimulus, a magnetic stimulus, and an ultrasonic stimulus.

A stress-free treatment method comprises the stimulus method.

An stimulus evaluation method comprises a stimulus method, wherein the increase rate of the blood flow is used as an indicator of the stimulus evaluation.

In general, two systems will be activated if the stress is applied to a living organism. One of the systems is a sympathetic nervous system beginning at a ceruleus nucleus (locus ceruleus), wherein noradrenalin is secreted from nerve ends, and adrenalin is secreted from adrenal cortex.

The other system is a HPA system (hypothalamus*pituitary*adrenal axis), wherein CRH (corticotropine releasing hormone) secreted from a hypothalamus (nucleus paraventricularis) acts on the hypophysis, and ACTH (adrenocorticotropic hormone) secreted from the pituitary anterior lobe (adenohypophysis) acts on the adrenal cortex, whereby finally glucocorticoid (cortisol) is secreted from the adrenal cortex. The cortisol is considered as an index of mental/physical stress, and can be also measured from saliva. In this stimulus, salivary amylase, ACTH, and cortisol were decreased. It would appear that a normalization of a stress reaction system hormone takes place.

Cortisol controls carbohydrate, fat, and protein metabolism, and is an indispensable hormone for living organisms. Blood pressure and a blood sugar level are raised depending on the quantity thereof secreted by stress, and it affects various living organism functions such as an immune system (inflammatory suppression), that is, for example, causing a decline in the immune function, a blood circulatory system, and a metabolism system (sugar rebirth) (glyconeogenesis). Furthermore, there is a receptor of the cortisol in a hypothalamus, a hippocampus, and a hypophysis, and if the amount of secretion of the cortisol increases, the amount of synthesis of CRH or ACTH decreases. As a result, the cortisol secretion is suppressed. Moreover, in recent years, there have been a report, as an index, based on MRI etc. of the brain of a patient with a PTSD (posttraumatic stress disorder), in which when the cortisol is secreted so much due to excessive stress, it atrophys the hippocampus. Thus, the cortisol also affects a central system (cognition, memory, emotions), and prevention of dementia, etc. can be expected by using an acupuncture needle stimulus.

A substance, which attracts attention together with the cortisol, is DHEA. The DHEA is a steroid hormone secreted from an adrenal cortex as well as the cortisol. It has been reported that the action is opposite to the cortisol. For example, although the cortisol suppresses Th1 immunity activity (NK cells, killer T cells) and facilitates Th2 immunity activity (B cells), DHEA facilitates the Th1 immunity activity conversely. Moreover, it is thought that patients with depression have a high cortisol level and have a low DHEA level, and a ratio thereof (cortisol/DHEA ratio) is important. It is considered that DHEA is a hormone which adjusts an action of the cortisol well.

Moreover, DHEA-sulfate (sulfate group-bound DHEA: DHEAS) (sulfate group bound form) is also thought to be important. Unlike the cortisol, there is no negative feedback as to DHEA, and if it is secreted, it is changed into DHEAS and accumulated, for a comparatively short time. Although the DHEAS itself has no activity as a hormone, the DHEAS is changed into DHEA in an organ which serves as a target, and acts on the target organ. The DHEAS is considered as an index showing a stable state of the DHEA. The DHEA and DHEAS are considered to have relation with stress.

It is considered that there are mechanism due to vasodilatation and mechanism under influence on sympathetic nerves by such stimulus. The action of the dilatation of vessel is considered to increase production of calcitonin gene-related peptide (CGRP) by the stimulus. It is thought that discharge of the CGRP etc. is increased due to an increase in muscle blood flow when nerves etc. are stimulated by the stimulus. Namely, efferent autonomic nerves or motor nerves are not included in a dorsal spinal nerve root. It is thought that axon-reflex mechanism arises due to a stimulus of afferent nerves etc., and CGRP is discharged from an end thereof, and it is based on the mechanism which a blood vessel of a governed area is dilated.

Furthermore, the influence on an autonomic nerve activity, which governs a blood vessel, is also assumed. Blood vessels of muscles are governed by adrenergic sympathetic nerves and cholinergic sympathetic nerves. The former is vasoconstrictor nerves through an alpha-receptor, and the latter is vasodilator nerves through acetylcholine. It is said that even at rest the former always works for the blood vessels of muscle in a state of tonus thereof, so that the blood vessels are always maintained in a coarctation state to some extent. On the other hand, as to the latter, it is thought that unstriped muscles of a blood vessel are relaxed in response to acetylcholine discharged from the end of nerves, so that the blood flow volume increases.

When the stimulus by acupuncture needles or warm temperature heating maintains parasympathetic nerve predominance, a long-term sympathetic nerve sthenia status is improved, so that it is also considered that there is a possibility that suppression of a RA system in a kidney is facilitated. This improves a hypertensive patient's QOL.

Furthermore, continuous stimulus treatment such as acupuncture needles and warm temperature heating showed a tendency of reduced insulin. It is thought that it is based on a continuous improvement of insulin resistance rather than an increase of a temporary insulin secretion. Moreover, obesity is one of the most important risk-factors of IGT. Harris et al. have epidemiologically showed the relation of the IGT and DM, and the obesity, in which that degree of obesity and an increase in weight play a major role in pathogenesis of DM. Therefore, it is thought that an improvement of the obesity problem leads to prevention of DM and also hypertension. In a medical interview, weight reduction of about 2 kg/month on average was confirmed.

Furthermore, in view of a rise in core body temperature and blood pressure change, etc., it is thought that the stimulus of acupuncture needles, warm temperature heating, etc. adjusts the blood flow of each organ through systemic blood pressure and autonomic nerves. It is thought that there is an effect of acupuncture needles, which are exerted on the systemic blood pressure, that an acupuncture needle stimulus causes a reaction to the systemicity through the sympathetic nerves.

A laser Doppler tissue blood flow meter ALF21D (manufactured by Adovans) is used to measure blood flow on a living tissue. In the laser Doppler tissue blood flow meter ALF21D, when a living tissue is irradiated with semiconductor laser light (whose wavelength is 780 nm), light reflected from the tissue is converted into an electric signal and the electric signal is processed, thereby obtaining information of the blood flow.

A C type laser probe (10 mm in diameter, 3 mm in thickness, 2 $mm^2$ in a laser irradiation area, and 1 mm in measurement depth) of the laser Doppler tissue blood flow meter was attached to a central part of a wrist joint horizontal line, and was measured, taking a 15-minute rest after a stimulus. A warm temperature heating probe is attached between bone heads of second and third metacarpal bones. And from measurement of the blood flow, an increase rate of the blood flow was calculated.

As to the principle of the laser Doppler tissue blood flow, laser light collides with red blood cells, which flow through the inside of a blood vessel, and the Doppler shift (frequency change), which is produced when receiving dispersion, is used. This measurement method is characterized by non-invasive and real time responsiveness and a capability of consecutive measurement. Furthermore, the ALF21D, which was used this time, could display a blood flow on ml/min/100 g scale. This is because signal processing is performed based on the theory of Bonner et al.

Description of the mechanism of an increase in a blood flow in a stress free treatment will be given below. A mental stress to a living body stimulates sympathetic nerves through the cerebral limbic system and hypothalamic pituitary, thereby constricting blood vessels and impairing the microcirculation system including internal organs of the living body. In the "stress free treatment" in response to a blood flow reduction response, a rise in body temperature of peripheral subcutaneous part at distances of 3 mm and 5 mm and, secretion control of stress hormone (amylase, cortisol, and ACTH) have been confirmed.

Furthermore, Vasoactive Intestinal Peptide (VIP) which is a living body activity hormone accelerates an intestinal peristalsis which is secreted from an alimentary canal, a pancreas, and a hypothalamus, and increases a blood flow including that of the alimentary canal etc. Moreover, vascularization and vascular permeability of microvessel are accelerated by a vascular endothelial growth factor (VEGF). It is considered that since the VIP and VEGF significantly increase by the "stress free treatment," both action of the VIP and that of the VEGF were induced, so that the blood flow of internal organs and peripheral blood flow were increased.

From these results, it is considered that with respect to sympathetic nerve activity through the autonomic nerves by the stress stimuli to a living body and overreaction of hypothalamohypophysial tropic hormones, the "stress free treatment" by thyroid stimulus acts on hypothalamus ascendence in an ascending manner, and while discharge of stress hormone is suppressed, the blood flow was increased through the VIP and VEGF.

Moreover, if a noxious stimulus such as stress and a pain is added to a living body, a finger tip cutis blood flow decreases, and an asympathetic flow response (SFR) appears. This reaction is evaluated by an index based on a peripheral blood flow as a reaction through a sympathetic nervous system against the noxious stimulus. In the stress free treatment, a blood flow at a central part of a wrist joint horizontal line increases, according to a laser Doppler tissue blood flowmeter, and it would appear that a reduction reaction of a blood flow, which mediates sympathetic flow response (SFR) by stress, increases a blood flow through the VIP and VEGF by the "stress free treatment" together with the depression effect of stress hormone.

Figure 2:
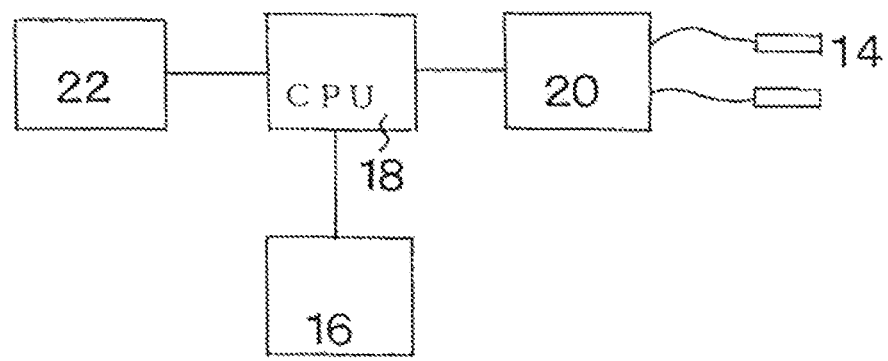
FIG. 2 is a schematic view of a circuit diagram of an electric type heating apparatus.

FIG. 1 is a schematic view of an electric type warm temperature heating apparatus used for the present invention. FIG. 2 is a schematic view of a circuit diagram of the electric type warm temperature heating apparatus.

A electric type warm temperature heating apparatus comprises the apparatus 10, and a guide element 14 for a thermal stimulus, which is connected to the apparatus 10 by a lead 12.

As shown, the apparatus 10 includes a memory unit 16, in which thermal stimulus patterns are stored, a control unit (CPU) 18, which reads out a thermal stimulus pattern from the memory unit 16, and an output unit 20, which supplies the thermal stimulus pattern to the guide element 14 for a thermal stimulus. A thermal stimulus is applied to a part to be stimulated, according to the thermal stimulus pattern.

A control unit (CPU) 18 is connected to the memory unit 16. A thermal stimulus pattern for obtaining a stimulus condition equivalent to that obtained from combustion of moxa is stored in the memory unit 16. The control unit (CPU) 18 reads out the thermal stimulus pattern from the memory unit 16, controls an output to a heating element(s) based on detection of a temperature sensor 22, and outputs the thermal stimulus pattern to the guide element(s) for a thermal stimulus.

The apparatus 10 is connected to two or more guide elements for a thermal stimulus in order to supply the thermal stimulus pattern to at least two different areas to be stimulated. In this manner, the thermal stimulus pattern is applied to the areas to be stimulated, through the guide elements for thermal stimulus.

A temperature sensor 22 is provided in a position(s) which is correlated with a temperature of an affected area near the heating elements. The guide elements for a thermal stimulus have a structure set forth below. The guide element 14 for a thermal stimulus, comprises a casing of apparatus 10, a heater which is provided in the casing, and is used as a source of warm temperature heating for applying thermal stimulus, a heat conduction board, which is provided on a lower face of the casing and which conducts heat of the heater to a skin of a patient, and a seal board provided on an upper face of the casing.

A heat conduction board of the guide elements for a thermal stimulus which are placed on two different areas, is desirably made up of at least two different kinds of metals. In this embodiment, aluminum and steel are used.

A temperature sensor is provided in a predetermined position of the housing which is in contact with a part of a human body, and detects the temperature of the position, so as to send a detection signal to a sensor amplifier. The control unit (CPU) controls an output of an electric power generating circuit so that the temperature of the portion, which is in contact with a skin surface of a human body contact, may not exceed a predetermined temperature. In the warm temperature heating apparatus, the surface temperature of the guide elements for a thermal stimulus is controlled so as to be in a range from 40 to 50±5 degrees Celsius.

When the heating temperature of the heating elements detected by the temperature sensor is equal to or lower than a reference temperature, a positive side period of a pulse signal is controlled so as to be long and a negative side period of the pulse signal is controlled so as to be short, according to the output of the temperature sensor. On the contrary, when it is in a state at the reference temperature, a positive side period is controlled so as to be short and a negative side period thereof is controlled so as to be long.

Figure 3:
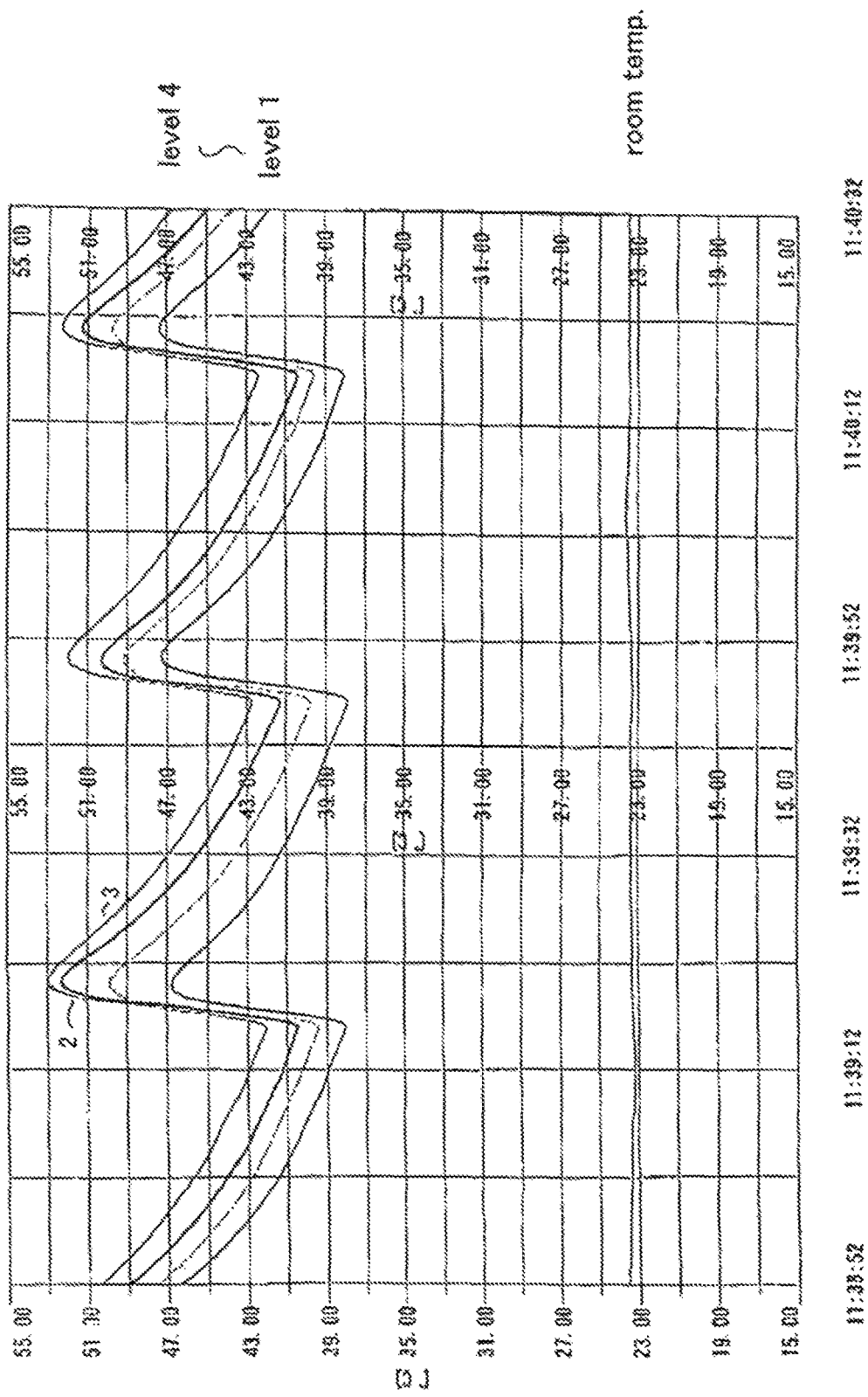
FIG. 3 is a schematic view of a thermal stimulus waveform obtained by controlling an electric type heating apparatus.

FIG. 3 shows a desirable thermal stimulus waveform, which is obtained by controlling the electric type warm temperature heating apparatus. The thermal stimulus waveform includes a heating waveform 2 obtained by heating it to a predetermined peak temperature, for example, 50±5 degrees Celsius, and a heat release waveform 3 which is formed by stopping heating after it reaches the peak temperature.

The heating waveform may be a convex shape heating waveform, an upward sloping line shape heating waveform, or a concave shape heating waveform. Moreover, the heating waveforms are not limited to the above-described heating waveform. It may be a saw-toothed shape waveform, and concavo-convex waveform. Moreover, the heating waveform and the heat release waveform may be formed as a sine waveform.

A cycle pattern of a thermal stimulus includes a thermal stimulus waveform made up of a warm heating waveform and a heat release waveform, and an interval before the next warm heating curve. One cycle pattern of the thermal stimulus is desirably set so that a thermal stimulus region may be 1 second to 30 seconds and an interval between the heating regions may be 1 second to 10 seconds.

The pattern of thermal stimulus desirably includes independent thermal stimulus waveforms whose phases are shifted so that the patterns of thermal stimulus do not substantially overlap each other. That is, as shown in the figures, the pattern of thermal stimulus includes a first thermal stimulus pattern including an interval between a thermal stimulus region and the next thermal stimulus region, and a second thermal stimulus pattern, which includes a thermal stimulus region during a certain period of an interval of the first thermal stimulus pattern and an interval in a first thermal stimulus region.

A cycle pattern of the thermal stimulus is desirably repeated for 10 minutes to 30 minutes. And, the cycle pattern of the thermal stimulus is desirably repeated again.

In addition, as a stimulus, an optical stimulus, a magnetic stimulus, an ultrasonic stimulus, a low frequency wave stimulus etc. may be used in addition to an acupuncture needle stimulus and a warm temperature heating stimulus.

Embodiment 1

Subjects were adult men and women. Burn injuries were taken into consideration so that an electric type warm temperature heating apparatus, MXA-8000 (SO-257), was used for a warm temperature heating stimulus. A probe thereof has a diameter of 10 mm, and a heating stimulus of warm temperature whose peak is 50±5 degrees Celsius was intermittently performed for 15 minutes. The probe was attached to the following warm temperature heating to the specific area to be stimulated of a body surface, and the specific areas was heated at 40 to 50 degrees Celsius.

Figure 4:
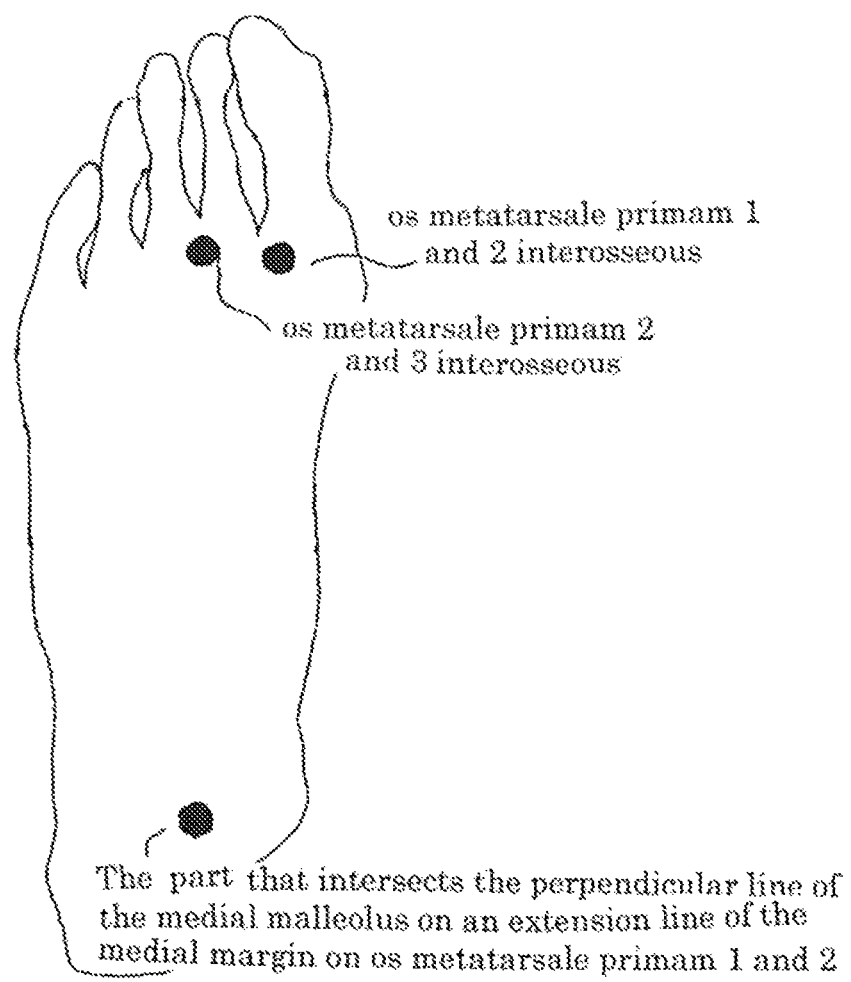
FIG. 4 is a schematic view of areas of a sole to be stimulated.

Here, the specific area to be stimulated is at least one selected from a group of os metatarsale primam 1 and 2 interosseous, os metatarsale primam 2 and 3 interosseous, or part that intersects the perpendicular line of the medial malleolus on an extension line of the medial margin on os metatarsale primam 1 and 2 in foot sole of right and left (refer to FIG. 4).

And a warm temperature heating stimulus is desirably applied to at least one specific area to be stimulated non-simultaneously and independently depending on the condition of disease.

Table 1 shows a result of blood flow measured at before and after of the stimulus at a central area of a wrist joint horizontal line by using a laser Doppler tissue blood flow meter, and the increase rate of blood flow. Wherein a warm temperature heating stimulus is applied at least one selected from a group of os metatarsale primam 1 and 2 interosseous, os metatarsale primam 2 and 3 interosseous, or part that intersects the perpendicular line of the medial malleolus on an extension line of the medial margin on os metatarsale primam 1 and 2 in foot sole of right and left as specific area to be stimulated.

TABLE 1

| Patient | stimulation before | stimulation after | increase rate |
|---------|--------------------|--------------------|---------------|
| No. 1   | 1.287              | 2.1036             | 63            |
| No. 2   | 3.2791             | 8.0098             | 144           |
| No. 3   | 1.7603             | 2.959              | 68            |
| No. 4   | 2.8101             | 4.6872             | 68            |
| No. 5   | 5.9857             | 13.0065            | 117           |
| No. 6   | 3.453              | 6.9631             | 102           |
| No. 7   | 2.0954             | 4.7401             | 126           |
| No. 8   | 1.4332             | 3.5227             | 146           |
| No. 9   | 1.0091             | 1.7377             | 72            |
| No. 10  | 3.9592             | 8.0699             | 104           |
| No. 11  | 1.5635             | 3.8743             | 148           |

As shown in the Table 1, the effects of the treatment were remarkable when the increase rate of the blood flow was 60% or more, and preferably 100% or more. At least one specific area to be stimulated, which are different from each other, are selected. The increase rate of the blood flow is used as an indicator of the stimulus. The increase rate of the blood flow may be 60% or more, preferably, 100% or more. Also, the increase rate of the blood flow is used as an indicator in evaluation of the stimulus.

Taking into consideration influences on the psychological stress through autonomic nerves, after keeping the subjects at rest in a state of a dorsal position for 20 minutes, the blood pressure, core body temperature, salivary amylase, and HEARTRATER (artery age) are measured and a warm temperature stimulus is performed just for 15 minutes, and they are measured again immediately after the stimulus.

Figures 5, 6:
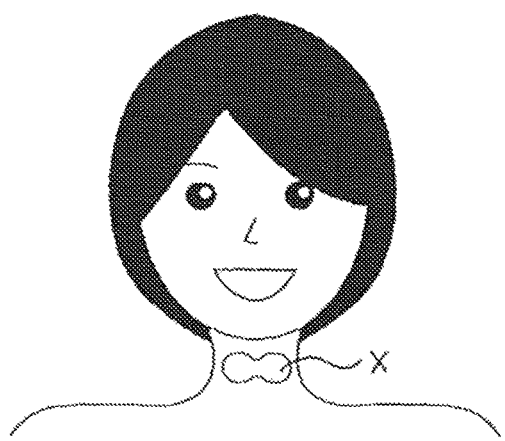
FIG. 5 is a schematic view of a protocol of a thermal stimulus.
FIG. 6 is a schematic view of an area near a thyroid gland to be stimulated.

The protocol of thermal stimulus is shown in FIG. 5. A treatment is made for the one time and the above-mentioned measurement is carried out before and after the treatment and next day thereto. A precapillary circulation which is innervated by an autonomic nervous system was measured by a deep body thermometer (a deep body temperature monitor, CORE TEMP CM-210 manufactured by TERUMO CORP.), and psychological stress is measured by DAEKI AMY (a salivary amylase monitor manufactured by NIPRO). Furthermore, an arteriosclerosis index and blood vessel age are quantified by HEARTRATER.

Blood is collected twice, that is, before the stimulus and at the same time one day after the stimulus, and a subject is refrained from consuming any food or liquid, except for water after 9:00 PM one day before the test and the test day.

Moreover, an advance explanation is made so that they refrain from undertaking strenuous forms of exercise from 24 hours before the test to one day after the test, and instructions are given to them to use a vehicle from home to a laboratory on the morning of the test day if possible, and to avoid intense activity and travel with minimum action.

It was observed that temperature rises in the area to be stimulated. It is noted that an increase in temperature was 2.1, especially when the stimulus was applied to os metatarsale primam 2 and 3 interosseous. As to salivary amylase, an increase tendency was shown when the stimulus was applied to os metatarsale primam 2 and 3 interosseous. The salivary amylase increase +34.25. Moreover, the cortisol is decreased −3.33 at os metatarsale primam 1 and 2 interosseous, and is decreased −6.33 at part that intersects the perpendicular line of the medial malleolus on an extension line of the medial margin on os metatarsale primam 1 and 2, When stimulus was applied to os metatarsale primam 1 and 2 interosseous, a significant decrease of systolic arterial pressure was −13.00.

When a stimulus was applied to os metatarsale primam 1 and 2 interosseous, a total cholesterol significantly is decreased −10.33. The neutral fat also is decreased −24.67 at part that intersects the perpendicular line of the medial malleolus on an extension line of the medial margin on os metatarsale primam 1 and 2. As to A.I. (arteriosclerotic index), when a stimulus was applied to to os metatarsale primam 1 and 2 interosseous, A.I. is decreased −0.10.

When a stimulus was applied to the area located at os metatarsale primam 1 and 2 interosseous; or os metatarsale primam 2 and 3 interosseous, the blood sugar level is decreased by −5.33 or 5.25. Furthermore, a hemoglobin A1c also decreased −0.13, when a stimulus was applied to os metatarsale primam 2 and 3 interosseous.

The amount of secretion of gastrin which is a gastrointestinal hormone was significantly increased 19.33 or 48.67, when a stimulus was applied to an os metatarsale primam 2 and 3 interosseous or part that intersects the perpendicular line of the medial malleolus on an extension line of the medial margin on an os metatarsale primam 1 and 2. This suggests that the digestive absorption and an intestinal peristaltic motion etc. increased.

When a stimulus was applied to an os metatarsale primam 1 and 2 interosseous, an Adiponectin is increased +1.5. Since the Adiponectin is considered as one of the substances which activates Sirtuin gene, and is one of genes relating to a long life, it was suggested that two stimuli to two areas of the plantar part turned ON the gene related to a long life.

When a stimulus is applied to an os metatarsale primam 1 and 2 interosseous, or part that intersects the perpendicular line of the medial malleolus on an extension line of the medial margin on os metatarsale primam 1 and 2, the leptin is degrease −0.57 or −0.20. The leptin is called "starvation hormone," and a body can originally store fat in the body. It is said that at the present day, 95% of cause of obesity is caused by "leptin resistance" due to excess leptin. It is thought that the Dayez effect would be expected by adjusting the amount of secretion of this substance.

A balance of an autonomic nerve is measured by Heart regulator. A degree of an activity of an autonomic nerve is increased +28.33 at an os metatarsale primam 1 and 2 interosseous. A degree of an resistance of an autonomic nerve is increased +14.67 at os metatarsale primam 1 and 2 interosseous or +12.25 at os metatarsale primam 2 and 3 interosseous. An index of a stress is degreased −17.00 at an os metatarsale primam 1 and 2 interosseous. A degree of a fatigue is degreased −30.00 at an os metatarsale primam 1 and 2 interosseous.

Embodiment 2

In this embodiment, an example which gave the acupuncture needle stimulus was applied to an area near thyroid gland as the specific area to be stimulated (refer to FIG. 6). The thyroid gland is an internal organ which is located in a shallow position from the body surface, and is observed at the depth in a range of approximately 5 mm-30 mm. Therefore, in general, an examination is performed by using a high frequency superficial probe in an ultrasonographic examination. The long diameter of the thyroid gland is approximately 40-50 mm, the thickness thereof is approximately 12-18 mm, the width diameter thereof is approximately 15-25 mm, and the thickness of isthmus thereof is approximately 2-4 mm.

The Acupuncture was performed for a total of ten men and women between the ages of 20 and 60 years old who have diagnosed as high blood pressure. Expecting influence action to psychological stress which is mediated by autonomic nerves, a disposable acupuncture needle (which was made of stainless steel, was 40 mm in length, and was thickness of 0.18 mm) was inserted to anterior neck region at a depth of 2-3 cm. After keeping subjects, who were examined, at rest in a state of a dorsal position for 15 minutes, blood pressure, core body temperature, and salivary amylase thereof were measured. And then the acupuncture needle stimulus was applied to them for 15 minutes, and they were measured again immediately after the needle was got out. The treatment was performed seven times, that is, 3 days after the first day, 7 days thereafter, 10 days thereafter, 14 days thereafter, 17 days thereafter, 21 days thereafter, In EMBODIMENT 2, the blood flow may be measured at before and after of the stimulus at a central area of a wrist joint horizontal line by using a laser Doppler tissue blood flow meter. And the same result as Table 1 of EMBODIMENT 1 may be obtained.

Effects

Values of alivary amylase, the highest and the lowest blood pressure showed significant decreased by the acupuncture needle stimulus. On the other hand, the core body temperatures at distances of 3 mm and 5 mm also showed the significant rise.

As for the salivary amylase, an increase was observed in +35. It is thought that since there were subjects who always had a high psychological stress among subjects with hypertension, the removal thereof decreased the pressure. There was a tendency in which systolic arterial pressure and diastolic blood pressure of the subjects decreased −13, when the acupuncture treatment continued. It was observed that subjects to whom hypotensor is not administered, rise in blood pressure immediately after the acupuncture treatment. Subjects, who were low in core body temperature at distances of 3 mm and 5 mm, greatly rose in the deep core temperature +2, and it was observed that the core body temperature converged at normal body temperature on the whole. Moreover, there was a tendency in which core body temperature before the acupuncture treatment became high, when the acupuncture treatment continued.

When the acupuncture treatment continued, the amount of secretion of cortisol and further that of ACTH which was a higher center thereof, decreased remarkably, immediately after the acupuncture needle treatment was performed on zero day, It was observed that it decreased after going up gently thereafter. Although the cortisol and ACTH of all the subjects transiently decreased, immediately after the acupuncture needle treatment was performed, and then the gradual increase tendency was shown, it was observed that there was a tendency in which it decreased when the treatment continued.

It was shown that there was a tendency to gently decrease in T-CHOL, HDL-CHOL, and LDL-CHOL.

Embodiment 3

In this embodiment, moxa cautery was performed on an area between an outer skin and a horizontal line on an inner border part of hallux distal phalanx bottom of left and/or right foot and phalanx proximalis in foot sole of right and left as a specific area to be stimulated.

Figure 7:
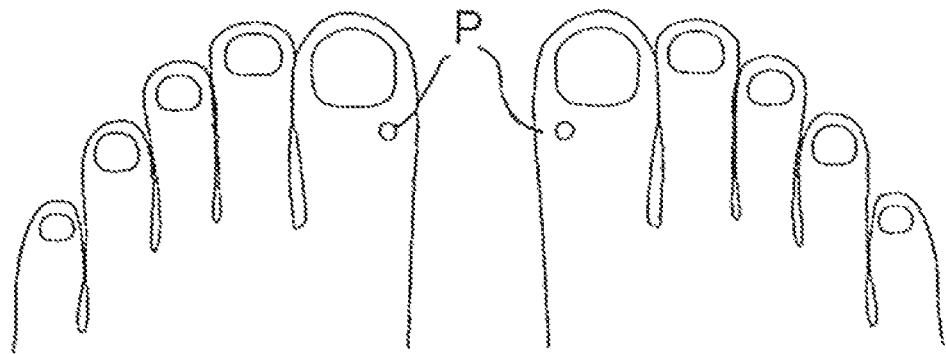
FIG. 7 is a schematic view of an area of a toe of a leg to be stimulated.
Figure 8:
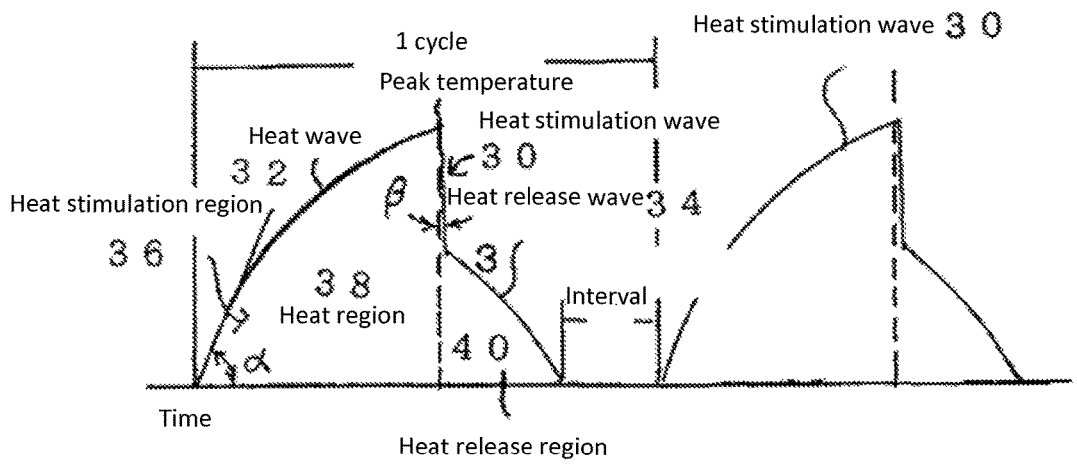
FIG. 8 is a diagram illustrating a waveform pattern applied in the thermal stimulus method according to Embodiment 4.
Figure 9:
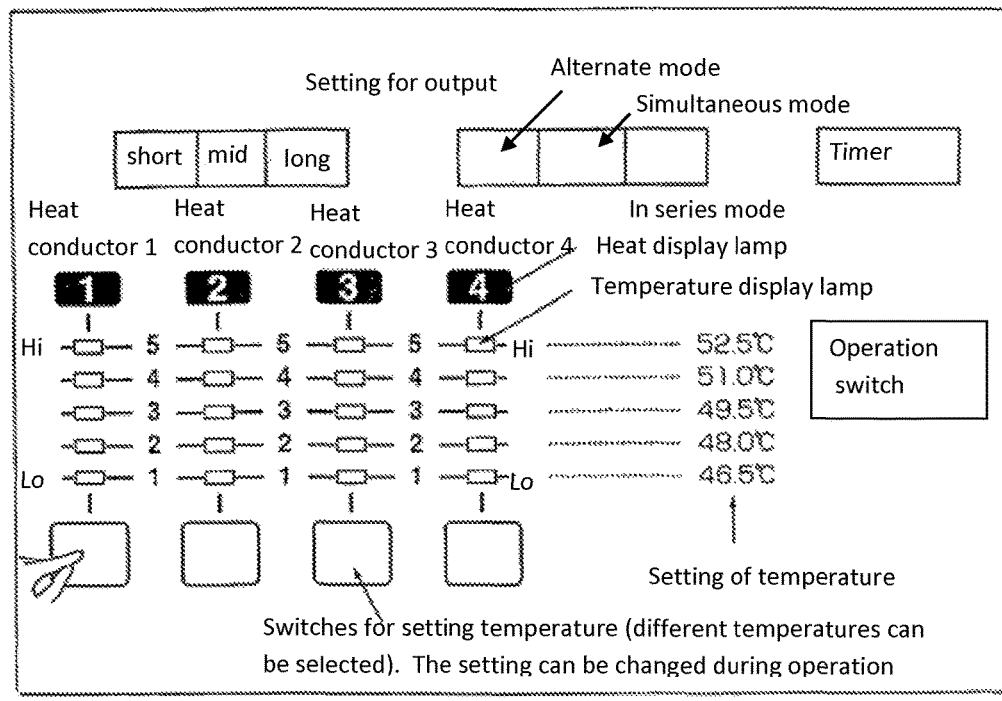
FIG. 9 is a schematic view of an apparatus for applying the thermal stimulus according to one embodiment according to the present invention.

In FIG. 7, a symbol "○" shows a specific area to be stimulated between the outer skin and a horizontal line of the inside boundary part of a hallux distal phalanx bottom and a proximal phalanx bone head, and applies a stimulus.

The moxa was applied to subjects by using pre-rolled moxa. The moxibustion was continuously performed five times respectively area between the outer skin and a horizontal line of the inside boundary part of a hallux distal phalanx bottom and a proximal phalanx bone head, and applies a stimulus.

The quantity of moxa per one moxibustion is 0.002 g, and the combustion temperature was 80±5 degrees Celsius at maximum. Two sets of treatments, which were performed in the beginning of week and the end of week, were repeated three times, that is, the treatment was performed six times in total.

It was confirmed from clinical data that secretion of thyroid hormone was activated by applying stimulus to area between the outer skin and a horizontal line of the inside boundary part of a hallux distal phalanx bottom and a proximal phalanx bone head, and applies a stimulus.

In EMBODIMENT 3, the blood flow may be measured at before and after of the stimulus at a central area of a wrist joint horizontal line by using a laser Doppler tissue blood flow meter. And the same result as Table 1 of EMBODIMENT 1 may be obtained.

Thereby, a rise in core body temperature, and prevention and improvement of obesity, diabetes, etc. is achieved. Therefore, it is thought that the treatment is one of the effective ways for a therapeutic procedure to lifestyle-related diseases, such as diabetes and obesity. Especially, explanation will be given below with respect to clinical data of a rise in core body temperature, diabetes and obesity on which remarkable effects were shown.

It was performed for a total of nine men and women between the ages of 20 and 60 years old who have diagnosed as diabetes, obesity and high blood pressure. Stimulation was applied by moxibustion to parts between the outer skin and the horizontal line of an inner border of hallux distal phalanx bottom of left and/or right foot and phalanx proximalis.

As described above, there are effects of a rise in core body temperature, a reduction of neutral fat, a reduction of cholesterol, a reduction of insulin, and suppression of arteriosclerosis.

It is preferred to perform the stimulus treatment to least one of the specific area to be stimulated selected from a group of EMBODIMENT 1 or EMBODIMENT 2 or The preceding description has been presented only to illustrate and describe exemplary embodiments of the present stimulus method for releasing stress, and stress-free medical treatment method by the stimulus method. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope.

Embodiment 4

In another aspect of the present application, the stimulus treatment described in the present application can be utilized to regulate immune cells. This method can be performed utilizing the apparatus described above and illustrated in accompanying drawings.

Treatment to Regulate Immune Cells

The followings are examples of body sites which can be stimulated by the stimulus treatment and results of the stimulations.

Ken Gu Ketsu or Jianyu points: location) the corner of the shoulder, the recessed part between the front edge of the outer periphery of hump and the greater tubercle of humerus.

Figure 11B:
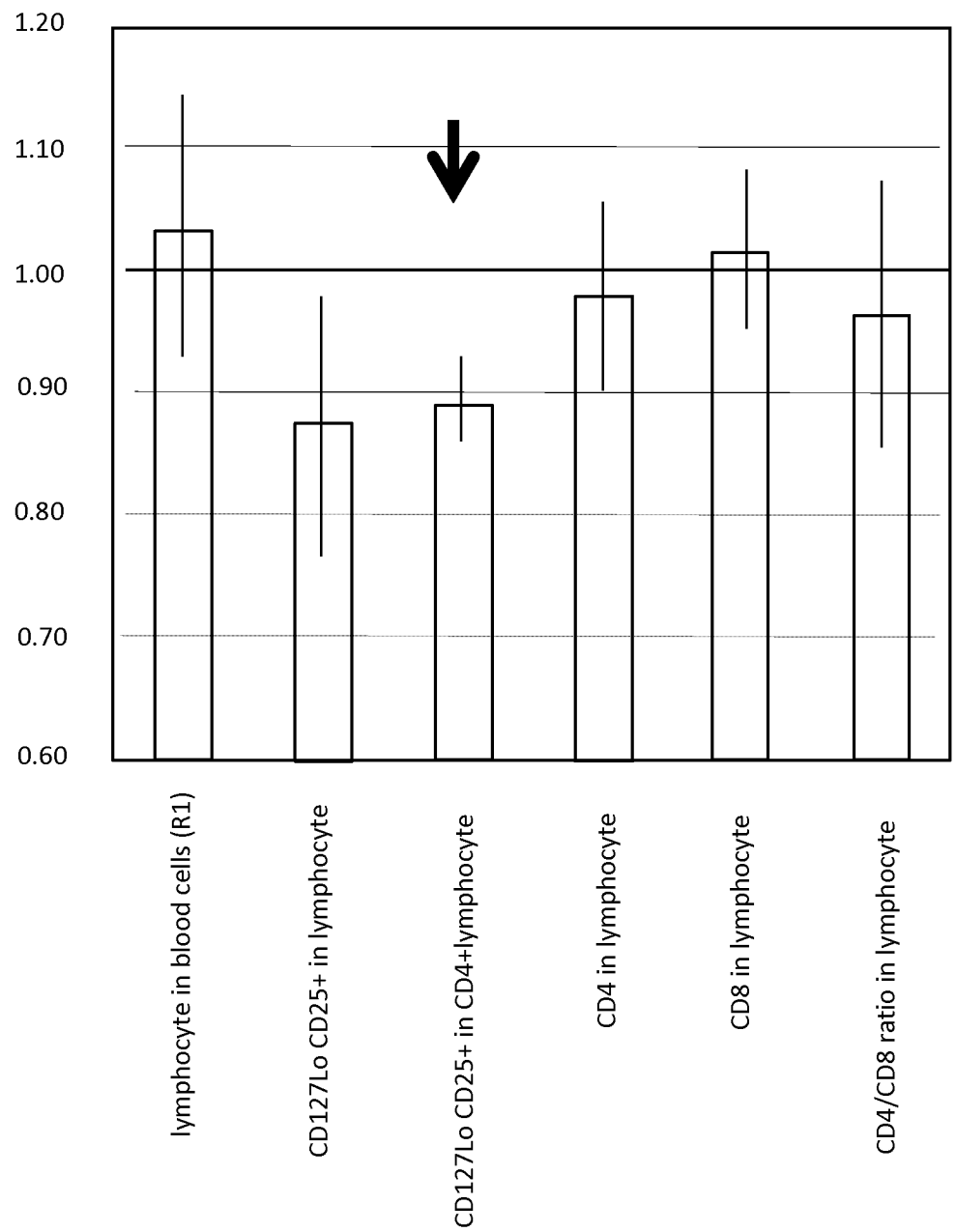

Results; it was observed that T reg. cells in CD4+ T lymphocytes significantly decrease by about 10%. As shown in FIGS. 11A and 11B, in stimulating Tsu-in, left legs Sanri, and both legs F points at the same time, the immunity system did not significantly change. It was observed that in the patients at the age of 32 or younger, T reg. cells in CD4+ T lymphocytes decrease. Since the lymphocytes in leucocytes and the T cell ratio did not vary, it is suggested to be specific to CD4+ T reg. cells.

Jin Gei Ketsu or Renying points: location) the same height as the regio cervicales anterior and the upper edge of thyroid cartilage, the front edge of sternocleidomastoid, on the common carotid artery.

Figure 15B:
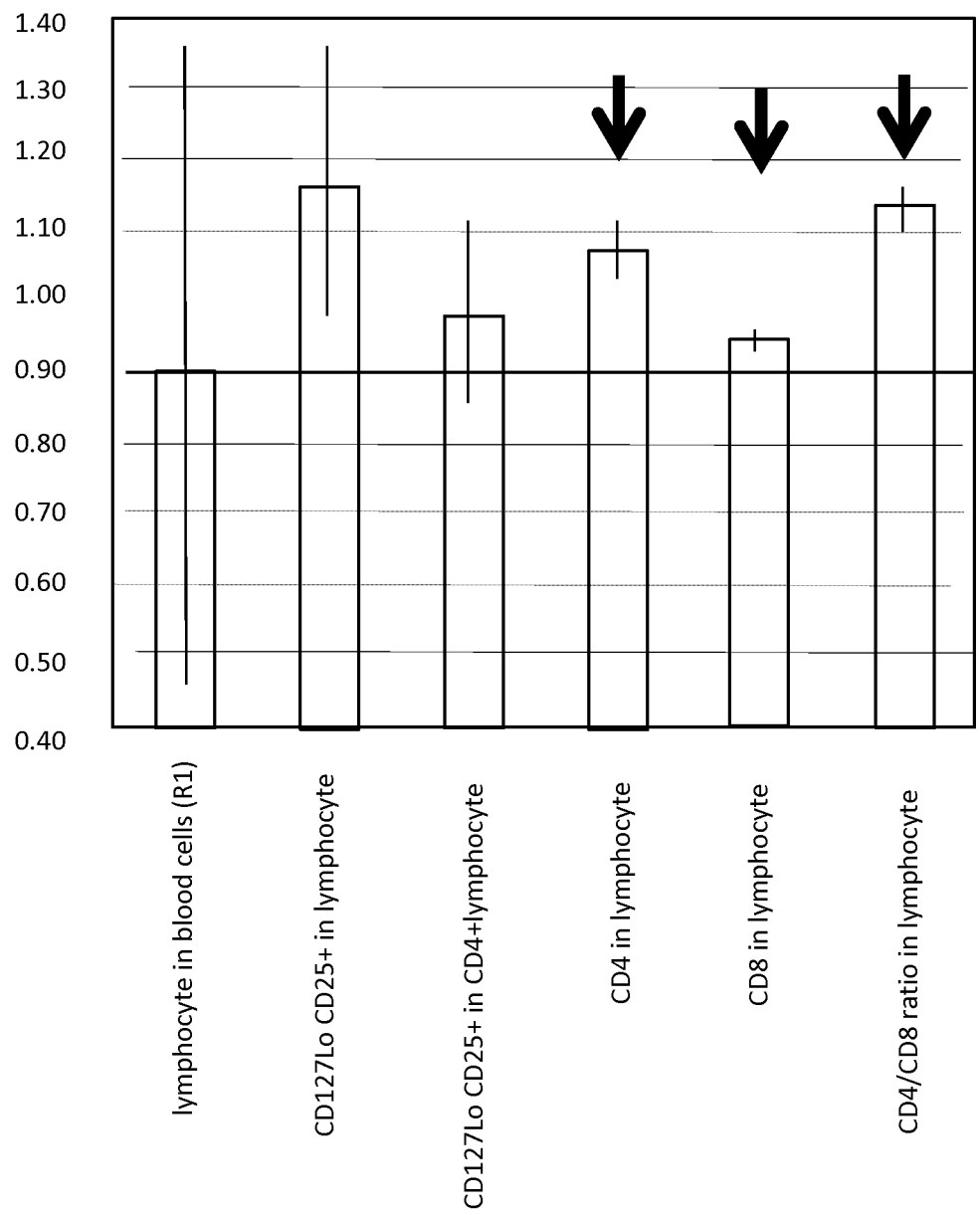

Results; it was observed that CD4+ T lymphocytes increase, while CD8+T lymphocytes decrease and that the CD4/CD8 ratio significantly increases by 10% or more. As shown in FIGS. 15A and 15B, since all patients are 30 years old or younger, if the blood (cardiovascular) system potentially has some problems resulting from aging, different alterations would be overserved.

Show Kai Ketsu or Zhaohai points: location) the margo medialis pedis, 3.3 cm below the top of Malleolus medialis, the recessed part below the Malleolus medialis.

Figure 12B:
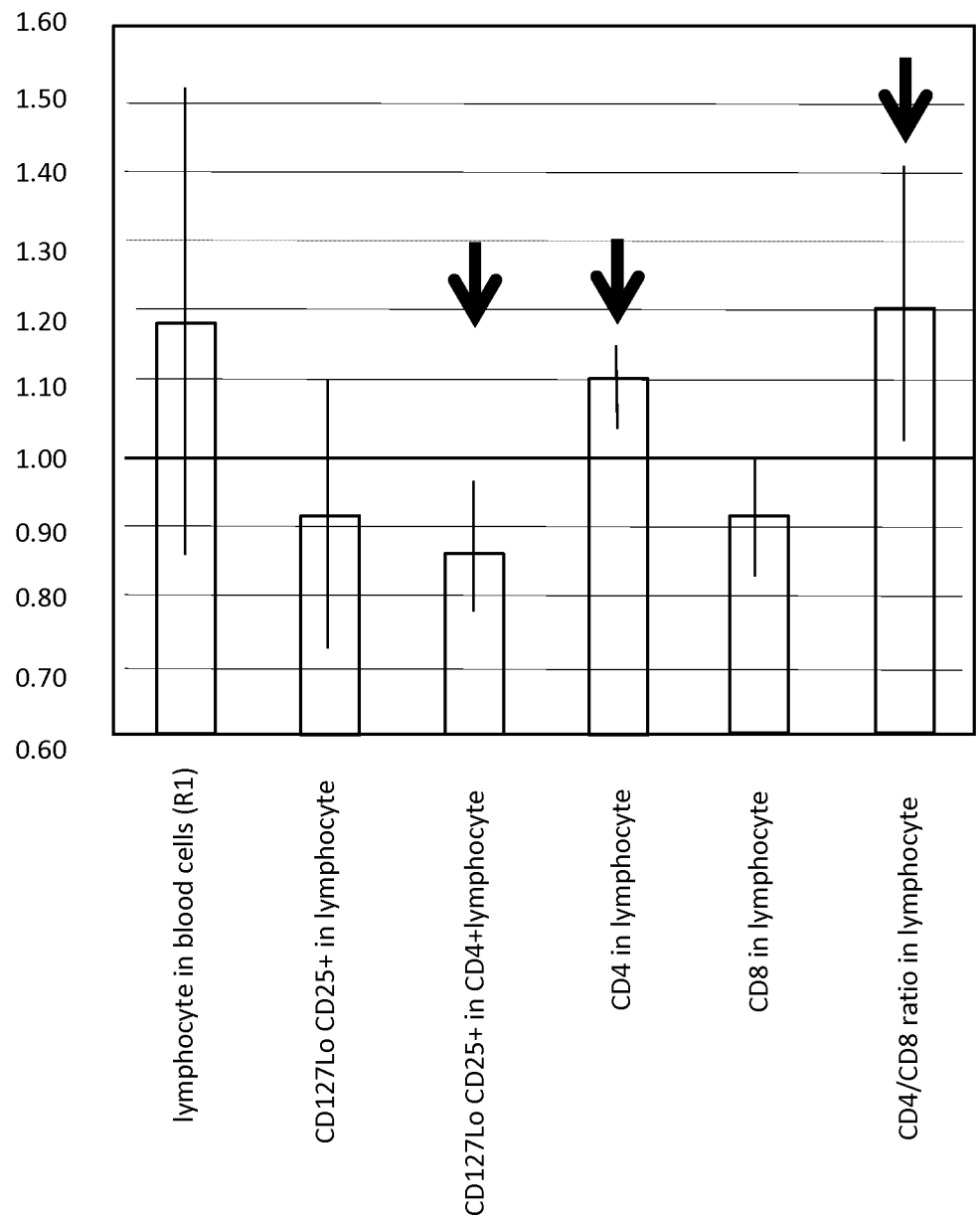

Results; it was observed that CD4+ T lymphocytes increase, while CD8+ T reg. cells decrease. As shown in FIGS. 12A and 12B, regardless of the ages, similar results were observed in all three patients. It is suggested that among CD4+ T lymphocytes, cells other than T reg. cells slightly increase.

San In Kou or Sanyinjiao points: location) the inside of lower legs (tibia side), around the back of the inner edge of tibia, 3.3 cm above the top of Malleolus medialis.

Figure 16B:
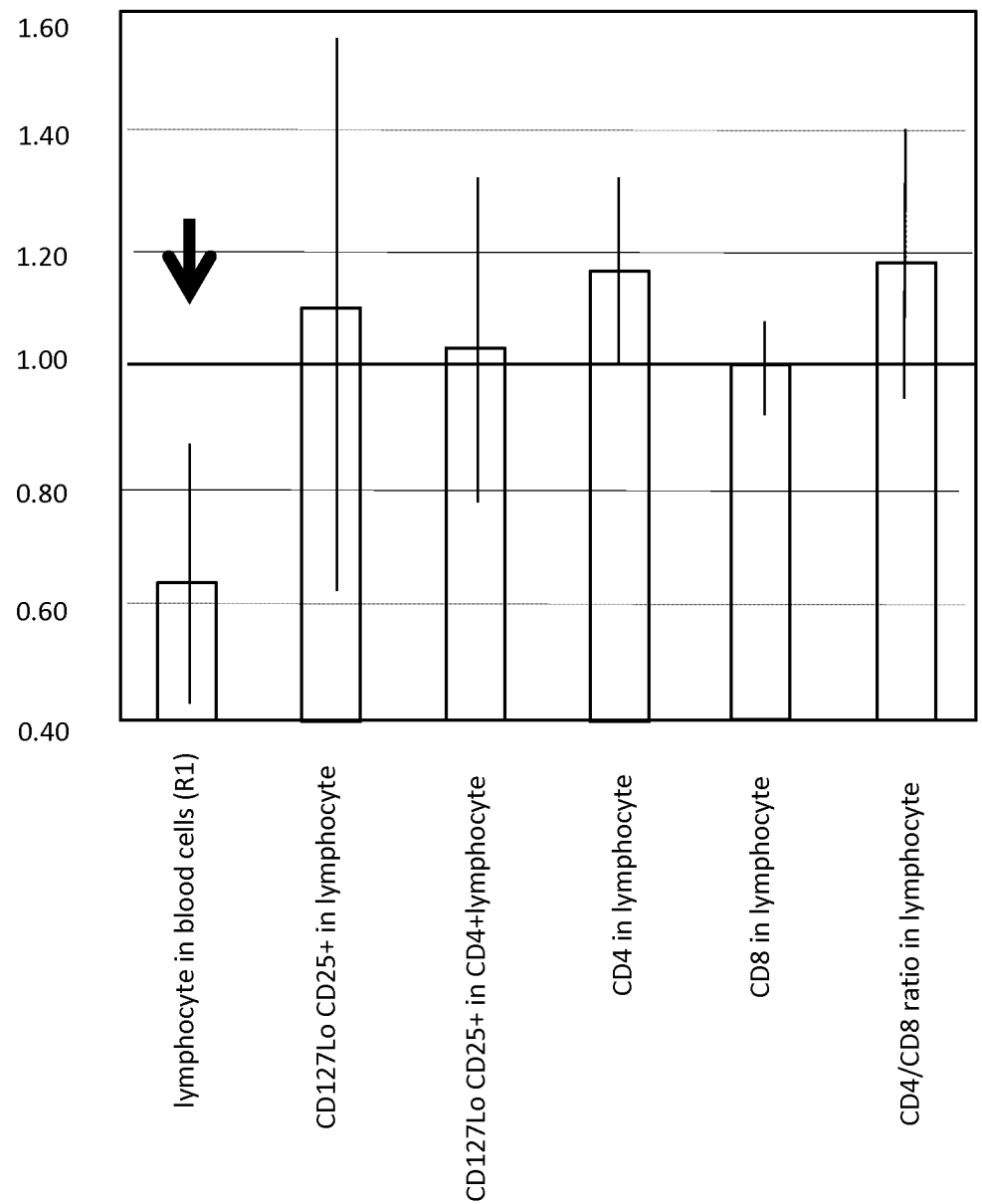

Results; it was observed that the lymphocytes ratio in leucocytes significantly decrease by 20% or more. As shown in FIGS. 16A and 16B, regardless of the ages, similar results were observed in all three patients. No significant alteration was observed in T reg. cell ratio in the lymphocytes or CD4+ T lymphocytes, CD8+ T lymphocyte ratio. It is suggested that differentiation of all lymphocytes in the bone marrow is suppressed in relation to the other cells.

Shi In Ketsu or Zhiyin points: location) the fifth finger of the legs, the outer side of distal phalanx.

Figure 13B:
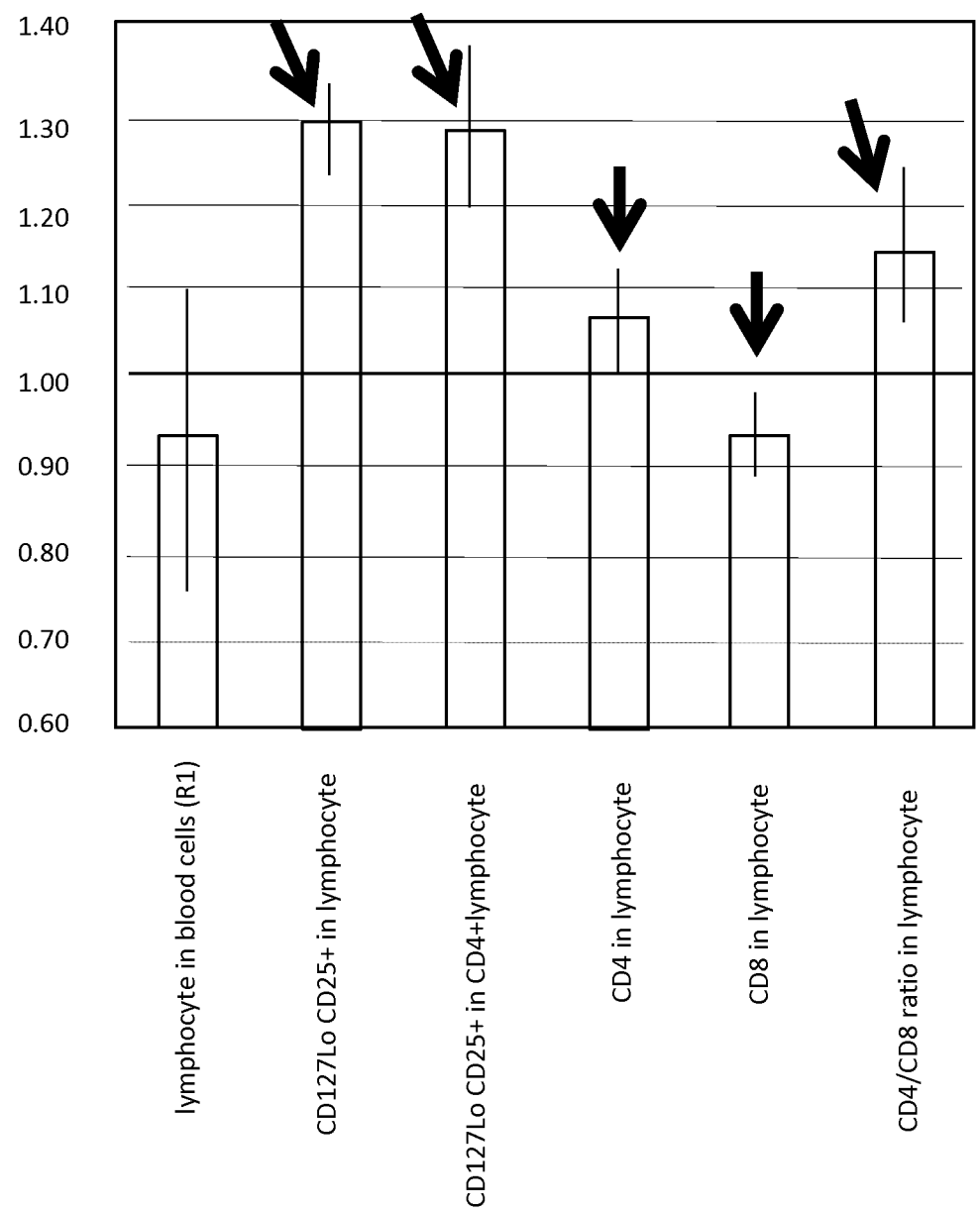

Results; it was observed that CD4+ T lymphocytes slightly increase, while CD8+T lymphocytes decrease and that CD4+ T reg. cells significantly increase by 30% or more. As shown in FIGS. 13A and 123B, it was observed that in the patients at the age of 40 or younger, CD4+ T reg. cells tend to remarkably increase. The increased amount of CD4+ lymphocytes and the increased amount of CD4+ T reg. cells are similar to each other. It is suggested that this alteration occurred due to the increase of CD4+T reg. cells.

Ken Show Ketsu or Xuanzhong points: location) the outer side of lower legs, the front side of fibula, 3.3 cm above the top of Malleolus lateralis.

Figure 14B:
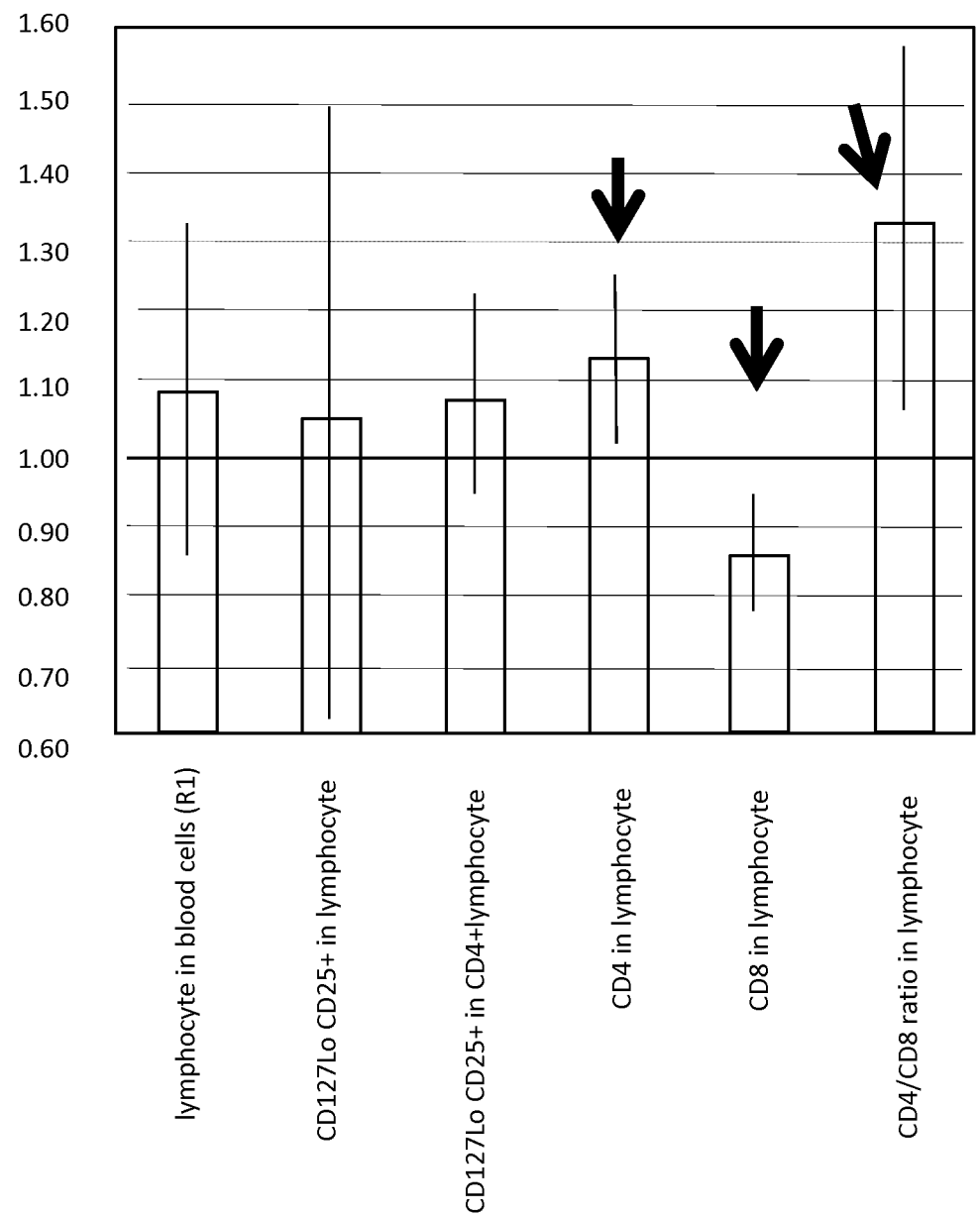

Results; it was observed that CD4+ T lymphocytes slightly decrease, while CD8+ T reg. cells decrease. As shown in FIGS. 14A and 14B, similar results were observed in all patients (at the age of 20 or younger). No alteration in T reg. cells was observed.

Chu Kyoku Ketsu or Zhongji points: location) at the center of the body.

Figure 10B:
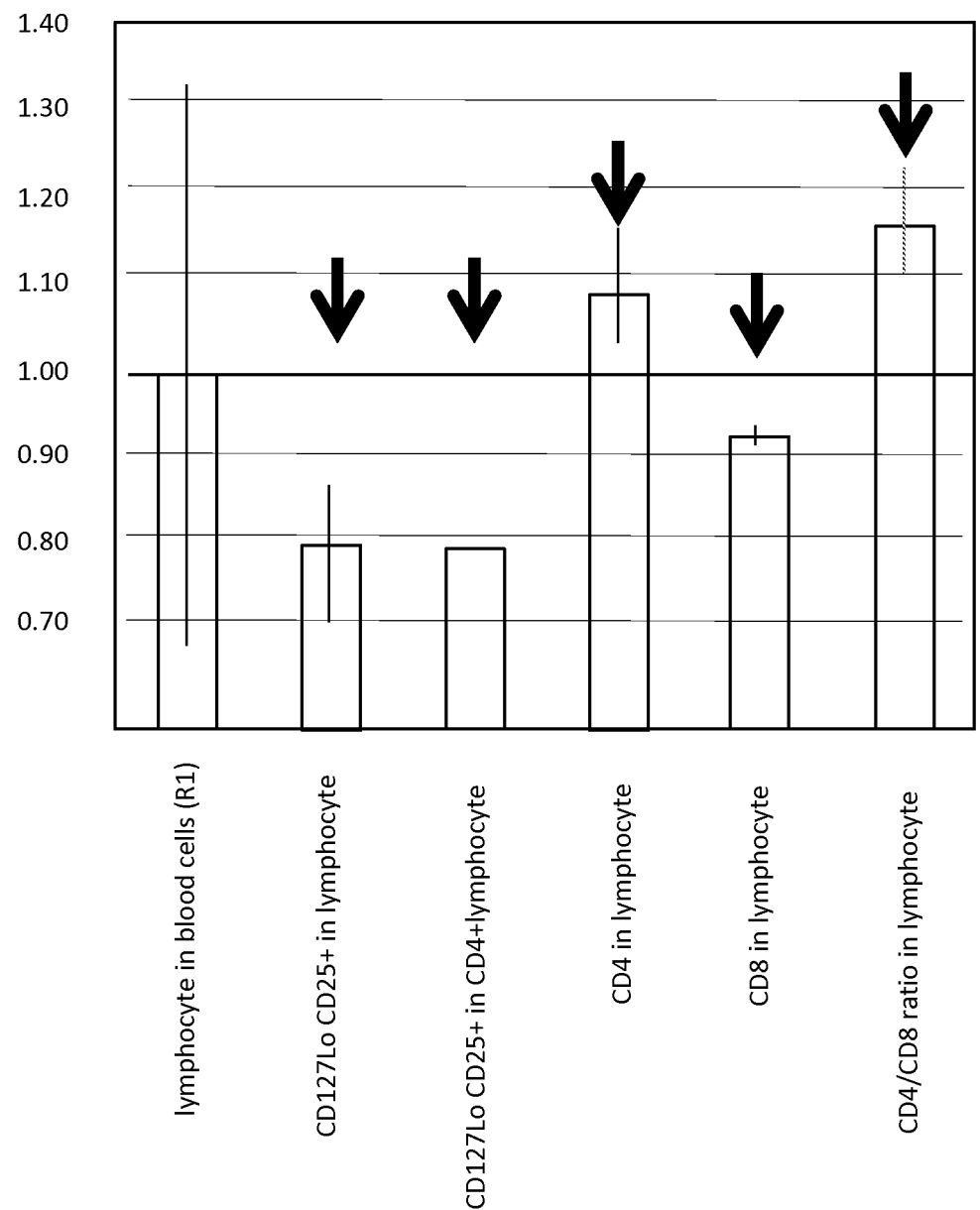

Results; it was observed that CD4+ T lymphocytes slightly increase, while CD8+ T reg cells decrease and that T reg. cells significantly increase by 20%. As shown in FIGS. 10A and 10B, for the patients at the age of 44 or younger, it was observed that T reg. cells significantly decrease. The data of CD4+ T reg. cells varied. The decrease of CD8+ lymphocytes and the decease of T reg. cells correspond to each other. It is suggested this alteration and variation occurred around CD8+ T reg. cells.

In this method, the regulation of immune cells can be performed by applying a stimulus to a specific area to be stimulated at a body surface by a stimulus applying apparatus so as to bring an increase rate of blood flow to 60% or more, preferably, 100% or more, wherein the blood flow is measured by a laser Doppler tissue blood flow meter attached to a central part of an inner side of a wrist joint, wherein regulating and balancing these T cell groups finely is essential to maintain the immune system of human beings and increase in blood flow volume by thermal therapy enables the "regulatory T cell" (or T-reg cell) to regulate and balance the immune cells.

In addition or alternatively, this method may regulate immune cells by performing the steps of contacting a thermal application terminal with at least two different body sites of the body surface to apply the thermal stimulation to the body sites, controlling the thermal stimulation in a manner that increases the blood flow by the application of the thermal stimulation to the body sites, in which the control of the thermal stimulation includes forming a thermal stimulation pattern with a thermal stimulation waveform and a heat release waveform. The thermal stimulation wave form is controlled to have a peak temperature which heats up the surface of the thermal application terminal to be in the range of 40 degrees Celsius to 50±5 degrees Celsius, and the heat release waveform is controlled to stop the heating after the peak temperature is achieved. The thermal treatment on at least two body sites with the thermal application terminal can be performed in different thermal application modes (operations) which include an alternative mode and a consecutive mode, whereby the thermal stimulation can be controlled to increase the blood flow by 60% to 150% before the treatment. The blood flow is measured by a laser Doppler tissue blood flow meter attached to a central part of an inner side of a wrist joint.

In the method for regulating immune cells, the specific area is at least one area selected from a group of os metatarsale primam 1 and 2 interosseous, os metatarsale primam 2 and 3 interosseous, and part that intersects the perpendicular line of the medial malleolus on an extension line of the medial margin on os metatarsale primam 1 and 2 in foot sole of right and left.

The thermal stimulation method is designed to increase the blood flow, thereby regulating the immune cells effectively. This method ultimately provides health benefits as explained below.

The immune system of human beings cannot function normally without a fine balance centering on these T cell groups. A thermal therapy according to the present invention reduces stress hormone such as cortisol with 100 percent reproducibility. In addition, immediately after the thermal therapy, two to four times increase in blood flow is provided.

Simultaneous appearance of VEGF (vascular endothelial growth factor) and VIP (vasoactive intestinal peptide) results in regeneration of inner walls of a blood vessel, enhancement of blood permeability, and improvement of blood flow. It is considered that these contribute significantly to migration property and normalization of immune cells in blood.

The body of a human being constantly fights unlimited variety of foreign foes such as pathogen, foreign substance, and parasite. A system for protecting the body against such foreign foes is referred to as "immunity." The "immune cells" are responsible for the immune system.

The "immune cells" include various types of cells depending on the function, such as, detecting a foe invading the body, notifying an invasion by the foe, directing to start an attack, and signaling start and finish of the attack. Each of them has their own responsibilities, and communicates with each other to work as a team.

Major immune cells are monocyte, lymphocyte (including T cell and B cell), and granulocyte, which circulates throughout the bloodstream and are collectively referred to as "leukocyte." If a blood test performed while a person has a cold, an inflammation inside the body, or other diseases, a high leukocyte count may be observed. This is because immune cells are activated against an abnormality inside the body.

These immune cells maintain the immune function by moving freely throughout the bloodstream. It is obvious that the sticky blood and bad bloodstream reduce each function.

In addition, immune cells communicate with each other and act by releasing a protein referred to as cytokine. Increased density and viscosity of blood lead to a loss of migration property of these proteins, and consequently, inherent communicative function is seriously impaired.

Necessity for a Long Life

The human body exists surrounded by foreign substances such as pathogen, harmful chemical substance, virus, and parasite. The human immune system against the foreign substances is a perfect system that ensures self-tolerance while fighting the foreign substances and foreign foes Thus, it can be said that the best thing is to normalize the inherent system in human beings.

How Immune Cells are Generated

Leukocyte as well as erythrocyte that delivers oxygen and platelet that stops bleeding circulate throughout the bloodstream. These are quite different from each other in appearance and function; however, these are generated from a common hematopoietic stem cell. A parent cell that can change to various types of cells is referred to as "stem cell." A process by which the cell changes from one cell type to another in property and function is referred to as "differentiation." Further, a process by which the cell gains specific function to get prepared to work is referred to as "maturation." The number of hematopoietic stem cells is very small as compared to total number of cells. However, during the course that the stem cells differentiate into immune cells, immune cells proliferate to a large number of immune cells. The hematopoietic stem cells are found in a liver in fetal life and then found in a bone marrow after birth. The hematopoietic stem cells derived from the bone marrow differentiate into "B cell" (an abbreviation for Bursa) mainly in gut-associated lymphoid tissue. On the other hand, when hematopoietic stem cells migrate to thymus above heart, they differentiate into T cells. The immune cells thus differentiated from the hematopoietic stem cells are delivered to a site where an immunoreaction is generated, such as lymph node and spleen, by the blood, and further differentiate repeatedly to mature into functional immune cells. A site where the stem cells first differentiate into immune cells, such as bone marrow and thymus, is referred to as "primary lymphoid tissue," and a site where an immunoreaction is generated is referred to as "secondary lymphoid tissue."

Two Trillion Immune Cells Protect the Body

It is said that the number of immune cells in adults is approximately two trillion. The immune cells protect 60 trillion cells in the human body. Immune cells circulate throughout the body by the bloodstream, and fight foreign foe with skillful teamwork. A macrophage responds to foreign foe invading the body first. When the macrophage finds a foreign substance, it traps expeditiously and engulfs them, and presents fragment of the foreign substance as an "antigen" to the T cell. T cells as a commander determine whether the foreign substance is a target for an attack, and then give a command. At first, T cells divide and release various activated molecules. The activated molecules include a factor for stimulating B cells. On the other hand, B cells recognize antigens with receptor on their cell surface (immunoglobulin). Subsequently, B cells initiate a proliferation and a division upon receiving a signal from T cells, and differentiate into antibody-producing cells (plasma cells) that generate a large number of antibodies.

In summary, T cells and B cells work in a coordinated manner with recognizing each other. "To recognize antigens" is a similar manner to recognize a human face by the difference in eyes, a nose, a mouth, and ears. Similarly, each antigen has a slightly different size and surface, so B cells recognize the difference. An antibody thus generated can respond to only one specific antigen. An antibody finds an antigen, and reacts with and binds to it to suppress its action while circulating throughout a body by the bloodstream. It is considered that antibodies have a capability of recognizing as many as 1010 antigens. In fact, the body of a human being has an immune system that can distinguish more than 10 billion foreign substances. Immunity fights off antigens by such exquisite system, and then B cells that have been produced antibodies die upon the completion of their role. However, not all B cells die, but some of the B cells remain in the body as memory B cells. These remaining B cells remember the "face" of the antigen firmly to produce the antibody expeditiously in preparation for being invaded by the same foe again. This is referred to as "immunological memory". It is said that once an individual is affected by "measles," the individual will never be affected by the same pathogen, because when the pathogen invades the body again, memory B cells respond to it expeditiously and produce a large number of antibodies instantly to kill it.

Tolerant System

Successive attack of immune cells as described above that is initiated by command and made in succession is strong defense system on high alert. However, the immune system that protects a human body by attacking and eliminating foreign foe must be regulated not to attack the body's own tissues. This is expressed as "be tolerant to one's self" in the field of immunology. Tolerance is allowance for and acceptance of others. That is to say, immunity must be a system which ensures that it does not target one's self for attack (=be tolerant to one's self) while eliminating foreign substances, and thus, discrimination between one's self and non-self is necessary for the function of this system. This is referred to as "Immune Tolerance." A main role in this discrimination is performed by a T cell. A surface of the T cell has a "T cell antigen receptor" (TCR: T-cell receptor) for discriminating a large number of foreign foes, which is used to recognize foreign substances. Each T cell has its own TCR, thereby allowing them to respond to any foreign substances expeditiously. This is the identity of T cells that cannot be seen in other types of cells. An antigen receptor TCR can be recombined in any form. In particular, TCR gene segments are shuffled to create combinations of TCR in 1010 ways. Such recombination of TCR allows the T cell to have near infinite discrimination capability. However, a random combination also creates cells targeting one's self for attack. Thus, an exquisite system—referred to as negative selection—that eliminates such harmful cells exists in thymus. In thymus, when an inappropriate or failed TCR is found, they are destroyed and eliminated instantly. It is said that 1% or less of T cells are able to pass this strict check. Selecting only harmless T cells not attacking one's self is referred to as "positive selection." The human body is thereby protected. However, the thymus rapidly degenerates into fat tissue upon reaching adulthood. Therefore, it is believed that autoimmune disease, which one's own immune cell attacks the own body, is more likely to be developed.

Types of T Cells

A method for regulating immune cells by increasing blood flow using thermal therapy according to the present invention is described below in detail. A description for T cells playing a central role in immune function is provided below. A T cell that involves in interaction with other immune cells required to produce antibody is referred to as a "helper T cell" (also referred to as CD4-positive T cell). A helper T cell divides into Th1, Th2, and Th17 that are named based on initials of T-cell helper, depending on the production pattern of cytokine that is a signal to other cells. A helper T cell also signals to a cell referred to as a "killer T cell" (or "cytotoxic T cell") that finds and starts a direct attack against foreign substances. On the other hand, a "regulatory T cell" (or T-reg cell) monitors and regulates overall immunoreaction so as not to overproduce antibodies or not to produce adverse antibodies to one's self. Thus, a regulatory T cell plays an important role necessary in order for the immunity of the human body to have tolerance to one's own tissues. In the case of autoimmune disease in which antibodies attacking one's self are produced, it has been frequently reported that the number of regulatory T cells decrease. Whereas, excessive increase in the number of regulatory T cells causes degradation in function for producing antibodies, and then overall immunocompetence is weakened. Regulating and balancing these T cell groups finely is essential to maintain the immune system of human beings. Increase in blood flow volume by thermal therapy according to the present invention enables the "regulatory T cell" (or T-reg cell) to regulate and balance the immune cells.

All Diseases are Autoimmune Disease

Allergies are various adverse effects caused by vital response of immune system against foreign substances from outside. It is recognized that most of the increasing various diseases including pollinosis, which is already considered to be national disease, are allergic disease or autoimmune disease. Despite being said that great strides are made in medical science, the cause of depression and dementia that can be a representative example of modern disease remains to be identified, and the cause of irreversible disorder (disorder from which individual cannot be recovered once it progressed), such as prostatic hyperplasia and knee osteoarthritis, is also unknown. However, these diseases have a common factor. The common factor is the presence of debris (=deposit). For example, in the case of Alzheimer's disease that is a representative disease of dementia, a phenomenon that β amyloid accumulates in the brain is well known. It is also well known that in the case of knee osteoarthritis, debris accumulate in joint. It is assumed that similar phenomenon can be observed in prostatic hyperplasia. A decrease in blood flow underlies the phenomenon. The decrease in blood flow results in poor circulation, and then generates debris. In the case of knee osteoarthritis, it is considered that a reduction of synovial fluid derives from the decrease in blood flow. In recent years, it has been found that Th17 cells of T cells play a central role in bone destruction of an articular surface that cause an arthrosis. T cells attack one's own tissues although T cells should be provider of immunity that protects the body.

Why does this Happen?

It is considered that the failure of the immune system including the T cell group due to the decrease in blood flow causes Th17 to attack one's own tissues. Observation of debris indicates the decrease in blood flow. Thus, when fine balance among T cell groups including helper T cells such as Th1 cells, Th2 cells, and Th17 cells, the killer T cell, and the regulatory T cell is lost, immune cells start attacking one's own tissues, that is to say, the autoimmune disease is caused. Furthermore, it is considered that most of diseases are autoimmune disease caused by similar processes. In particular, when helper T cells are overactivated, immune tolerance is disrupted and the brunt of an attack is directed to one's own tissues. On the other hand, when regulatory T cells are too predominant, immunocompetence is weakened, and thereby, onset of infection and cancer is triggered. The immune system of human beings cannot function normally without a fine balance centering on these T cell groups. A thermal therapy according to the present invention reduces stress hormone such as cortisol with 100 percent reproducibility. In addition, immediately after the thermal therapy, two to four times increase in blood flow is provided. Simultaneous appearance of VEGF (vascular endothelial growth factor) and VIP (vasoactive intestinal peptide) results in regeneration of inner walls of a blood vessel, enhancement of blood permeability, and improvement of blood flow. It is considered that these contribute significantly to migration property and normalization of immune cells in blood.

In addition, increase in blood flow volume by thermal therapy with electrical stimulation according to the present invention allows intentional regulation of increase in volume of an erythrocyte and hemoglobin concentration per an erythrocyte. This increases the water content of a cell and normalizes proliferation of a cell. Method for applying a stimulus to a specific area to be stimulated at a body surface by a stimulus applying apparatus so as to bring an increase rate of blood flow to 60% or more, preferably, 100% or more, wherein the blood flow is measured by a laser Doppler tissue blood flow meter attached to a central part of an inner side of a wrist joint is disclosed at the embodiment described above.

What is claimed is:

1. A method for regulating immune cells comprising:
applying a stimulus to a specific area to be stimulated at a body surface by a stimulus applying apparatus so as to bring an increase rate of a blood flow to 60% or more, preferably, 100% or more,
wherein the blood flow is measured by a laser Doppler tissue blood flow meter attached to a central part of an inner side of a wrist joint,
wherein the increase rate of blood flow by thermal therapy enables a regulatory T cell to regulate and balance the immune cells and regulating and balancing these T cell groups finely is essential to maintain the immune system of human beings, and
wherein the specific area is at least one area selected from the group consisting of os metatarsale primam 1 and 2 interosseous, os metatarsale primam 2 and 3 interosseous, and part that intersects the perpendicular line of the medial malleolus on an extension line of the medial margin on os metatarsale primam 1 and 2 in foot sole of right and left.

2. A method for regulating immune cells comprising;
contacting a thermal application terminal with at least two different body sites of a body surface to apply a thermal stimulus to the body sites; and
controlling the thermal stimulus to increase a blood flow by the application of the thermal stimulus to the at least two different body sites,
wherein the controlling of the thermal stimulus comprises forming a thermal stimulus pattern formed of a thermal stimulation wave form having a peak temperature which heats up a surface of the thermal application terminal to be in a range of 40 to 50° C.±5° C. and a heat release waveform to stop the heating after the peak temperature is achieved and applying the thermal stimulus pattern so as to increase the blood flow at the at least two different body sites stimulated by 60% to 150% as compared with the blood flow before the thermal stimulation,
wherein the blood flow is measured by a laser Doppler tissue blood flow meter attached to a central part of an inner side of a wrist joint, and
wherein the at least two different body sites comprise at least one area selected from the group consisting of os metatarsale primam 1 and 2 interosseous, os metatarsale primam 2 and 3 interosseous, and part that intersects the perpendicular line of the medial malleolus on an extension line of the medial margin on os metatarsale primam 1 and 2 in foot sole of right and left.

* * * * *